US007517883B2

(12) United States Patent
LaVoie et al.

(10) Patent No.: US 7,517,883 B2
(45) Date of Patent: *Apr. 14, 2009

(54) SOLUBILIZED TOPOISOMERASE POISONS

(75) Inventors: Edmond J. LaVoie, Princeton Junction, NJ (US); Alexander L. Ruchelman, Robbinsville, NJ (US); Leroy F. Liu, Bridgewater, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 7 days.

This patent is subject to a terminal disclaimer.

(21) Appl. No.: 11/210,456

(22) Filed: Aug. 24, 2005

(65) Prior Publication Data

US 2006/0052381 A1 Mar. 9, 2006

Related U.S. Application Data

(63) Continuation of application No. 10/846,834, filed on May 14, 2004, now Pat. No. 7,049,315, which is a continuation of application No. PCT/US02/36901, filed on Nov. 14, 2002.

(60) Provisional application No. 60/332,734, filed on Nov. 14, 2001.

(51) Int. Cl.
C07D 491/147 (2006.01)
C07D 491/22 (2006.01)
A61K 31/4738 (2006.01)
A61K 31/4985 (2006.01)
A61K 31/5025 (2006.01)
A61P 35/00 (2006.01)
A61P 17/06 (2006.01)

(52) U.S. Cl. .................. 514/248; 514/280; 514/250; 546/48; 544/233; 544/342

(58) Field of Classification Search ................. 514/248, 514/250, 280; 546/48
See application file for complete search history.

(56) References Cited

U.S. PATENT DOCUMENTS

| 2,915,523 | A | 12/1959 | Moore et al. |
| 2,981,731 | A | 4/1961 | Moore et al. |
| 2,985,661 | A | 5/1961 | Hien et al. |
| 3,267,107 | A | 8/1966 | Sallay |
| 3,272,707 | A | 9/1966 | Tedeschi |
| 3,449,330 | A | 6/1969 | Guglielmetti et al. |
| 3,538,097 | A | 11/1970 | Lowe et al. |
| 3,542,782 | A | 11/1970 | Houlihan et al. |
| 3,849,561 | A | 11/1974 | Junzo et al. |
| 3,884,911 | A | 5/1975 | Shimada et al. |
| 3,912,740 | A | 10/1975 | Zee-Chang et al. |
| 4,749,708 | A | 6/1988 | Maroko |
| 4,761,417 | A | 8/1988 | Maroko et al. |
| 4,761,477 | A | 8/1988 | Ikekawa et al. |
| 4,925,943 | A | 5/1990 | Kanmacher et al. |
| 4,980,344 | A | 12/1990 | Maroko |
| 5,106,863 | A | 4/1992 | Hajos et al. |
| 5,126,351 | A | 6/1992 | Luzzio et al. |
| 5,153,178 | A | 10/1992 | Maroko |
| 5,190,753 | A | 3/1993 | Behrens et al. |
| 5,244,903 | A | 9/1993 | Wall et al. |
| 5,318,976 | A | 6/1994 | Luzzi et al. |
| 5,639,759 | A | 6/1997 | Magolda et al. |
| 5,646,283 | A | 7/1997 | Suzuki et al. |
| 5,767,142 | A | 6/1998 | La Voie et al. |
| 5,770,617 | A | 6/1998 | LaVoie et al. |
| 5,807,874 | A | 9/1998 | LaVoie et al. |
| 5,981,541 | A | 11/1999 | LaVoie et al. |
| 6,140,328 | A | 10/2000 | LaVoie et al. |
| 6,486,167 | B1 | 11/2002 | LaVoie et al. |
| 6,509,344 | B1 | 1/2003 | Cushman et al. |
| 6,740,650 | B2 | 5/2004 | LaVoie et al. |
| 6,964,964 | B2 | 11/2005 | LaVoie et al. |
| 7,049,315 | B2 | 5/2006 | LaVoie et al. |
| 7,319,105 | B2 * | 1/2008 | LaVoie et al. ............... 514/280 |
| 2004/0102443 | A1 | 5/2004 | LaVoie et al. |
| 2004/0110760 | A1 | 6/2004 | LaVoie et al. |
| 2004/0110782 | A1 | 6/2004 | LaVoie et al. |
| 2005/0009824 | A1 | 1/2005 | LaVoie et al. |

(Continued)

FOREIGN PATENT DOCUMENTS

EP 0108147 B1 5/1984

(Continued)

OTHER PUBLICATIONS

Cecil Textbook of Medicine, edited by Bennet, J.C., and Plum F., 20th edition, vol. 1, 1004-1010, 1996.*

(Continued)

Primary Examiner—Venkataraman Balasubramanian
(74) Attorney, Agent, or Firm—Viksnins Harris & Padys PLLP

(57) ABSTRACT

The invention provides compounds of formula I:

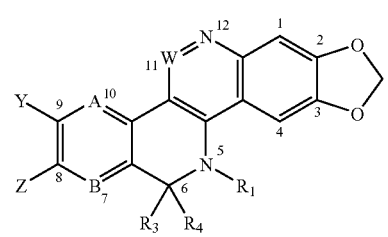

wherein

A, B, W, Y, Z, and $R_1$ have any of the meanings defined in the specification and their pharmaceutically acceptable salts. The invention also provides pharmaceutical compositions comprising a compound of formula I, processes for preparing compounds of formula I, intermediates useful for preparing compounds of formula I, and therapeutic methods for treating cancer using compounds of formula I.

32 Claims, No Drawings

U.S. PATENT DOCUMENTS

| | | |
|---|---|---|
| 2005/0009825 A1 | 1/2005 | LaVoie et al. |
| 2005/0009826 A1 | 1/2005 | LaVoie et al. |
| 2005/0010046 A1 | 1/2005 | LaVoie et al. |

FOREIGN PATENT DOCUMENTS

| | | |
|---|---|---|
| EP | 0496634 A1 | 7/1992 |
| GB | 2108955 A | 5/1983 |
| SU | 1530628 | 12/1989 |
| WO | WO-92/21661 A1 | 12/1992 |
| WO | WO-96/36612 A1 | 11/1996 |
| WO | WO-97/29106 A1 | 8/1997 |
| WO | WO-98/12181 A1 | 3/1998 |
| WO | WO-98/31673 A1 | 7/1998 |
| WO | WO-99/31067 A1 | 6/1999 |
| WO | WO-00/21537 A1 | 4/2000 |
| WO | WO-01/32631 A2 | 5/2001 |
| WO | WO-03/041680 A2 | 5/2003 |
| WO | WO-03/047505 A2 | 6/2003 |
| WO | WO-2004/014918 A1 | 2/2004 |

OTHER PUBLICATIONS

Denny, "Emerging DNA Topisomerase Inhibitors as Anticancer Drugs", *Expert Opin. Emerg. Drugs*, 9(1), 105-133 (2004).

Ruchelman et al., "Diaza- and Triazachrysenes: Potent Topoisomerase-Targeting Agents with Exceptional Antitumor Activity Against the Human Tumor Xenograft, MDA-MB-435", *Bioorganic & Medicinal Chemistry Letters*, 12, 3333-3336 (2002).

Ruchelman et al., "11H-isoquino[4,3-c]cinnolin-12-ones; Novel Anticancer Agents with Potent Topoisomerase I-Targeting Activity and Cytotoxicity", *Bioorganic & Medicinal Chemistry*, 12, 795-806 (2004).

Aguirre, J. M., et al., "Reactin of 1,2-diarylethylamides with ethyl polyphosphate(EPP): correlation of the von Braun, Ritter and Bischler-Napieralski reactions.", *Chemical Abstracts*, 111(13), Abstract No. 115004, (1989), 646.

Akiyama, Shin-Ichi , et al., "Isolation and Genetic Characterization of Human KB Cell Lines Resistant to Multiple Drugs", *Somatic Cell and Molecular Genetics*, 11(2), (1985), 117-126.

Andoh, Toshiwo, et al., "Characterization of a mammalian mutant with a camptothecin-resistant DNA topoisomerase I", *Proceedings of the National Academy of Sciences USA*, 84(16), (1987), 5565-5569.

Andoh, Toshiwo, et al., "Drug resistance mechanisms of topoisomerase I drugs", *Advances in Pharmacology*, vol. 29B, *DNA Topoisomerases: Topoisomerase- Targeting Drugs*, (1994), 93-103.

Arumugam, N., et al., "Synthesis of 7,8-Benzophenanthridines", *Indian Journal of Chemistry*, vol. 12, (1974), 664-667.

Badia, Dolores, et al., "Silicon-mediated isoquinoline synthesis: preparation and stereochemical characterization of 4-hydroxy-3-phenylisoquinolines", *Chemical Abstracts*, 117(13), Abstract No. 131034, (1992), 730.

Baezner, C., et al., "Uberfuhrung von o-nitro- und o,p-dinitrobenzylchlorid in acridinderivate", *Berichte der Deutschen Chemischen Gesellschaft*, 39, English Title—Conversion of o-nitro and o,p-dinitrobenzylchlroide into acridinic derivatives, (1906), 2438-2447.

Baezner, Carlo, "Uberfuhrung von o-nitro-und o, p-dinitrobenzylchlorid in acridinderivate", *Berichte der Deutschen Chemjschen Gesellschaft*, 37, English Title—Conversion of o-nirobenzyl chloride and o,p-dinitrobenzyl chloride into acridine derivatives, (1904), 3077-3083.

Bhakuni, D. S., et al., "Protoberberine Alkaloids", *The Alkaloids*, vol. 28, Chapter 2, Academic Press, Inc., (1986), 95-181.

Bjornsti, Mary-Ann, et al., "Expression of human DNA topoisomerase I in yeast cells lacking yeast DNA topoisomerase I: restoration of sensitivity of the cells to the antitumor drug camptothecin", *Cancer Research* 49, (1989), 6318-6323.

Bradsher, Charles K., et al., "alpha-Acyl-o-tolunitriles as intermediates in the preparation of 3-substituted isoquinolines and 1-amino-2-benzopyrylium derivatives", *Chemical Abstracts*, 89(21), Abstract No. 89: 179810b,(1978), 590.

Brossi, Arnold, "Benzo[c]phenanthridine Alkaloids", *The Alkaloids, Chemistry and Pharmacology*, vol. XXV, Academic Press, Inc., (1985), 178-199.

Buu-Hoi, N. P., et al., "Carcinogenic Nitrogen Compounds. XV. Polysubstituted Angular Benacridines and Benzophenarsazines", *Chemical Abstracts*, 49(1), Abstract, col. 330, 10-Organic Chemistry, (1955), 329-330.

Buu-Hoi, N. G., et al., "The Chemistry of Carcinogenic Nitrogen Compounds. Part X. The Pfitzinger Reaction in the Synthesis of 1:2-Benzacridines", *Journal of the Chemical Society*, Letchworth, GB, (1952), 279-281.

Buu-Hoi, N. G., "The chemistry of carcinogenic nitrogen compounds. Part V. Angular hydroxybenzacridines and hydroxydibenzacridines", *Journal of the Chemical Society*, Letchworth GB, (1950), 2096-2099.

Carmichael, James, "Evaluation of a tetrazolium-based semiautomated colorimetric assay: assessment of chemosensitivity testing", *Cancer Research*, 47, (1987), 936-42.

Chen, Allan Y., "A new mammalian DNA topoisomerase I poison Hoechst 33342: cytotoxicity and drug resistance in human cell cultures", *Cancer Research*, 53(6), (1993), 1332-1337.

Chen, Allan Y., et al., "DNA Minor Groove-Binding Ligands: A Different Class of Mammalian DNA Topoisomerase I Inhibitors", *Proceedings of the National Academy of Sciences of the United States of America*, 90, (1993), 8131-8135.

Chen, Allan Y., et al., "DNA Topoisomerases: Essential Enzymes and Lethal Targets", *Annu. Rev. Pharmacol. Toxicol.*, 34, (1994), 191-218.

Cherif, Abdallah, et al., "N-(5,5-Diacetoxypent-1-yi)doxorubicin: a new intensely potent doxorubicin analogue", *Journal of Medicinal Chemistry*, 35, (Aug. 21, 1992), 3208-3214.

Croisy-Delcey, M., et al., "Synthesis and Carcinogenic Activity of Oxidized Benzacridines: Potential Metabolites of the Strong Carcinogen 7-methylbenz[c]acridine and of the Inactive Isomer 12-methylbenz[a]acridine", *Chemical Abstracts*, 98, Abstract No. 43798, (1983), 27-29.

Croisy-Delcey, M. , et al., "Synthesis and carcinogenic activity of oxidized benzacridines: potential metabolites of the strong carcinogen 7-methylbenz[c]acridine and of the inactive isomer 12-methylbenz[a]acridine.", *Journal of Medicinal Chemistry*, 26, (1983), 303-306.

Cushman, Mark, et al., "Synthesis and antitumor activity of structural analogues of the anticancer benzophenanthridine alkaloid fagaronine chloride", *Journal of Medicinal Chemistry*, 2B, (1985), 1031-1036.

Cushman, Mark, et al., "Synthesis of New Indeno[1,2-c]Isoquinolines: Cytotoxic Non-Camptothecin Topoisomerase I Inhibitors", *Journal of Medicinal Chemistry* 43(20), (2000), 3688-3698.

D'Arpa, Peter, et al., "Topoisomerase-targeting antitumor drugs", *Biochimica et Biophysica Acta*, 989, (1989), 163-177.

Denizot, F., et al., "Rapid colorimetric assay for cell growth and survival. Modifications to the tetrazolium dye procedure giving improved sensitivity and reliability", *Journal of Immunological Methods*, 89, (1986), 271-277.

Dominguez, Esther, et al., "Dehydrogenation reactions of 1-substituted-3-aryltetrahydroisoquinoline derivatives", *Chemical Abstracts*, 101(11), Abstract No. 090742z,(1984),624.

Dorofeenko, G. N., et al., "Synthesis of 3-aryl derivatives of 2-benzopyrylium salts with free alpha-positions", *Chemical Abstracts*, 74 (15), Abstract No. 076295, (1971), 432.

Fitzgerald, J. J., et al., "Reaction of benzocyclobutene oxides with nitriles: synthesis of hypecumine and other 3-substituted isoquinolines", *Chemical Abstracts*, 122(7), Abstract No. 081704, (1995), 1128.

Fox, G. J., et al., "para-Bromination of Aromatic Amines: 4-Bromo-N,N-Dimethyl-3-(Trifluoromethyl)Aniline", *Organic Syntheses*, vol. 55, (1976), 20-23.

Fujii, Noboru , et al., "Induction of Mammalian DNA Topoisomerase I-mediated DNA Cleavage and DNA Winding by Bulgarein", *Journal of Biological Chemistry*, 268(18), (1993), 13160-13166.

Gallo, Robert C., et al., "Studies on the Antitumor Activity, Mechanism of Action, and Cell Cycle Effects of Camptothecin", *Journal of the National Cancer Institute*, vol. 46, No. 4, (1971), pp. 789-795.

Garcia, Alberto, et al., "A simple direct approach to 1-substituted 3-arylisoquinolines from deoxybenzoins and nitriles", *Chemical Abstracts*, 110(25), Abstract No. 231407u, (1989), 622.

Gatto, Barbara, "Identification of Topoisomerase I as the Cyctotoxic Target of the Protoberberine Alkaloid Coralyne", *Cancer Research*, 56(12), (1996), 2795-2800.

Giovanella, Beppino C., et al., "Complete growth inhibition of human cancer xenografts in nude mice by treatment with 20-(s)-camptothecin", *Cancer Research*, 51(11), (1991), 3052-3055.

Godowski, K. C., et al., "Free amine benzophenanthridine alkaloid compositions", USPATFULL Database, No. 95:20510 RN No. 218-38-2, (Benzo[c]phenanthradine), from U.S. Patent 5,395,615, (1995), 3 pages.

Goldman, Gustavo H., et al., "Differential poisoning of human and *Aspergillus nidulans* DNA topoisomerase I by bi- and terbenzimidazoles", *Biochemistry* 36(21), (1997), 6466-6494.

Gopinath, K. W., et al., "Synthesis of Some 1:2- and 7:8-Benzophenanthridines", *Journal of the Chemical Society*, 78(2), (1958), 504-509.

Hahn, F. E., et al., "Berberine", *In: Antibiotics, Mechanism of Action of Antimicrobial and Antitumor Agents*, vol. III, J.W. Corcoran, et al., (eds.), Springer-Verlag, (1975), 577-584.

Halligan, Brian D., et al., "Purification and Characterization of a Type II DNA Topoisomerase from Bovine Calf Thymus", *The Journal of Biological Chemistry*, 260(4), (1985), 2475-2482.

Hoan, Nguyen, et al., "Syntheses from o-halogenated anisoles and phenetoles", *Chemical Abstracts*, 41(20), American Chemical Society, Abstract No. 8571bg. (1947), 2 Pages.

Hsiang, Yaw-Huei, et al., "Identification of Mammalian DNA Topoisomerase I as an Intracellular Target of the Anticancer Drug Camptothecin", *Cancer Research*, 48(7), (1988), 1722-1726.

Iwao, Masatomo, et al., "A Regiospecific Synthesis of Carbazoles via Consecutive Palladium-Catalyzed Cross-coupling and Aryne-Mediated Cyclization", *Heterocycles*, 36, (1993), 1483-1488.

Izmail'skii, V.A., et al., "Absorption Spectra of Molecular Complexes of Derivatives of Benzacridine and Dibenzacridine", *Chemical Abstracts*, 54(8), Abstract, col. 7335b, (1960), 3 pages.

Jacob, Juergen, et al., "Monooxygenase Induction by Various Xenobiotics and its Influence on Rat Liver Microsomal Metabolism of Chrysene in Comparison to Benz[a]anthracene", *Chemical Abstracts*, 107, Abstract No. 34760, (1987), 2 p.

Janin, Yves L., et al., "Synthesis and Evaluation of New 6-Amino-Substituted Benzo[c]phenanthridine Derivatives", *Journal of Medicinal Chemistry*, 36(23), (1993), 3686-3692.

Jayaraman, M., et al., "Synthesis of New Dihydroindeno [1,2-c] isoquinoline and Indenoisoquinolinium Chloride Topoisomerase I Inhibitors Having High in Vivo Anticancer Activity in the Hollow Fiber Animal Model", *Journal of Medicinal Chemistry*, 45(1), (2002), 242-249.

Kametani, Tetsuji, et al., "Studies on the synthesis of heterocyclic compountds. DCXXVII. The formation of 2,3,9,10-tetramethoxybenz[c]acridine by treatment of 6,7-dimethoxy-1-(4,5-dimethoxy-2-nitrophenethyl)-2-methylisoquinoline with triethyl phosphite", *Chemical and Pharmaceutical Bulletin*, 23(9), (1975), 2025-2028.

Kametani, T., et al., "Synthesis of Heterocyclic Compounds. DCXXVII. Formation of 2,3,9,10-tetramethoxybenz[c]acridine by treatment of 6,7-dimethoxy-1-(4,5-dimethoxy-2-nitrophenethyl)-2-methylisoquinoline with Triethyl Phosphite", *Chemical Abstracts*, 84, Abstract No. 43798, (1976), 1 p.

Kanmacher, I., et al., "Synthesis of Isoquino[1,2-b]quinazolines by Cycloaddition Reaction", *Chemical Abstracts*, 114, Abstract No. 207191, (1990), 4 pages.

Kar, G. K., et al., "Regioselective Thermal Cyclization of 3-substituted Arylenaminoimine hydrochlorides. A convenient method for the synthesis of Functionalized Polycyclic Quinoline Derivatives", *Chemcial Abstracts*, 123, Abstract No. 111828, (1995), 1 p.

Kerrigan, J. E., et al., "5H-8,9-Dimethoxy-5-(2-N,N-dimethylaminoethyl)dibenzo[c, h][1,6]naphthyridin-6-ones and Related Compounds as TOP1-Targeting Agents: Influence of Structure on the Ternary Cleavable Complex Formation", *Bioorganic and Medicinal Chemistry Letters*, 13, (2003). 3395-3399.

Kessar, S V., et al., "Azasteroids. Part VII. Synthesis of 7-hydroxy-2-methoxy-7,8,9,10-tetrahydrobenzo[I]phenanthridine", *J. Chem Soc.*, (1971), 259-261.

Kessar, S. V., et al., "New Routes to Condensed Polynuclear Compounds: Part X-Synthesis of Some Benzo[i]phenanthridines through Benzyne Cyclization", *Indian Journal of Chemistry*, 11, (1973), pp. 624-627.

Kim, J. S., et al., "Influence of steric factors on topoisomerase I inhibiton and cytotoxicity of bisbenzimidazoles related to Hoechst 33342", *Proceedings of the 86th Annual Meeting of the American Association for Cancer Research*, 36, Abstract No. 2689, Toronto, Ontario, Canada, (Mar. 1995), p. 451.

Kim, J. S., et al., "Influence of steric factors on topoisomerase I inhibition and cytotoxicity of bisbenzimidazoles related to Hoechst 33342", *Abstract—Proceedings of the 3rd Annual Scientific Retreat of the Cancer Institute of New Jersey*, Princeton Marriott Forrestal Village, (1995), p. 28.

Kim, Jung S., et al., "Quantitative structure-activity relationships on 5-substituted terbenzimidazoles as topoisomerase I poisons and antitumor agents", *Bioorganic & Medicinal Chemistry*, 6(2), (1998), 4 pages.

Kim, J. S., et al., "Steric factors associated with the topoisomerase I inhibition and cytotoxicity of substituted bisbenzimidazoles", *Abstract 10- Proceedings of the American Association of Pharmaceutical Scientists Eastern Regional Meeting*, (1995), p. 27.

Kim, Jung S., et al., "Structure-activity Relationships of Benzimidazoles and Related Heterocycles as Topoisomerase I Poisons", *Bioorganic & Med. Chem.*, 4, (1996), pp. 621-630.

Kim, Jung S., "Substituted 2,5'-Bi-1 H-benzimidazoles: Topoisomerase I Inhibition and Cytotoxicity", *Journal of Medicinal Chemistry*, 39(4), (1996), 992-998.

Kim, Jung S., et al., "Terbenzimidazoles: influence of 2"-, 4-, and 5-substituents on cytotoxicity and relative potency as topoisomerase I poisons", *Journal of Medicinal Chemistry*, 40(18), (1997), 2818-2824.

Kitamura, Tsugio, et al., "Isoquinoline derivatives from the Ritter-type reaction of vinyl cations", *Chemical Abstracts*, 102(1), Abstract No. 6157c, (1985).

Klopman, Gilles, et al., "Testing by Artificial Intelligence: Computational Alternatives to the Determination of Mutagenicity", *Chemical Abstracts*, 118, Abstract No. 17489, (1993), 1 p.

Knab, A. M., et al., "Mechanisms of Camptothecin Resistance in Yeast DNA Topoisomerase I Mutants", *Journal of Biological Chemistry*, 268(30), (1993), 22322-22330.

Lavoie, E. J., et al., "Structure-activity studies related to minor groove-binding ligands which inhibit mammalian DNA topoisomerase I", *Abstract 1—Proceedings of the 85th Annual Meeting of American Association for Cancer Research*, San Francisco, CA, (Apr. 1994), p. 2699.

Lee, Jeremy S., et al., "Coralyne binds tightly to both T A T- and C G C+- containing DNA triplexes", *Biochemistry*, 32(21), (1993), 5591-5597.

Liu, Leroy F., et al., "Cleavage of DNA by Mammalian DNA Topoisomerase II", *Journal of Biological Chemistry*, vol. 258, No. 24, (1983), 15365-15370.

Makhey, Darshan, "Coralyne and Related Compounds as Mammalian Topoisomerase I and Topoisomerase II Poisons", *Bioorganic & Medicinal Chemistry*, 4(6), (1996), 781-791.

Makhey, Darshan, "Protoberberine Alkaloids and Related Compounds as Dual Inhibitors of Mammalian Topoisomerase I and II", *Medicinal Chemistry Research*, 5(1), (1994), 1-12.

Meegalla, Sanath K., et al., "Synthesis and Pharmacological Evaluation of Isoindolo[1,2-b]quinazolinone and Isoindolo[2,1-a]benzimidazole Derivatives Related to the Antitumor Agent Batracylin", *J. Med. Chem.*, 37, (1994), pp. 3434-3439.

Memetzidis, G., et al., "Structure-affinity relationships of berbines or 5,6,13,13a-tetrahydro-8H-dibenzo[a,g]quinolizines at alpha-adrenoceptors", *European Journal of Medicinal Chemistry*, 26, (1991), 605-611.

Messmer, F. M., et al., "Fagaronine, a New Tumor Inhibitor Isolated from Fagara zanthoxyloides Lam. (Rutaceae)", *Journal of Pharmaceutical Sciences*, (1972), 1858-1859.

Mohanty, N., et al., "New Therapeutic agents of the quinoline series. I. Fused quinolyl compounds", *Chemical Abstracts*, (1968), p. 1792.

Mosmann, Tim, "Rapid Colorimetric Assay for Cellular Growth and Survival: Application to Proliferation and Cytotoxicity Assays", *Journal of Immunological Methods*, 65(1-2), (1983), 55-63.

Nelson, Janis T., et al., "Proton and carbon-13 NMR spectra of fifteen substituted isoquinolines", *Chemical Abstracts*, 115(5), Abstract No. 048721, (1991), 753.

Peters, Dan, et al., "Synthesis of Various 5-Substituted Uracils", *Journal of Heterocyclic Chemistry*, 27, (Nov.-Dec. 1990), 2165-2173.

Pilch, Daniels S., et al., "A terbenzimidazole that preferentially binds and conformationally alters structurally distinct DNA duplex domains: a potential mechanism for topoisomerase I poisoning", *Proc. Nat'l. Acad. Sci. USA*, 94(25), (1997), 13565-13570.

Pilch, Daniel S., et al., "Biophysical Characterization of a Cytotoxic, Topoisomerase I Polson", *Abstract 8—Proceedings of the 3rd Annual Scientific Retreat of the Cancer Institute of New Jersey*, Princeton Marriott Forrestal Village, Princeton, NJ, (Jun. 1, 1995), 2 Pages.

Pilch, Daniel S., et al., "Characterizing the DNA binding modes of a topoisomerase I-poisoning terbenzimidazole: evidence for both intercalative and minor groove binding properties", *Drug Design and Discovery*, 13, (1996), 115-133.

Piper, J. R., et al., "Synthesis and Antifolate Activity of 5-Methyl-5, 10-dideaza Analogues of Aminopterin and Folic Acid and an Alternative Synthesis of 5,10-Dideazatetrahydrofolic Acid, a Potent Inhibitor of Glycinamide Ribonucleotide Formyltransferase", *J. Med. Chem.*, 31, (1988), pp. 2164-2169.

Porai-Koshits, B. A., et al., "Imidazole derivatives. IV. Synthesis of some polybenzimidazoles", *J. Gen. Chem. USSR*, 23, As related in Chemical Abstracts, 48 (10) (1954), Col. 12740, (1953), pp.873-879.

Quast, Ulrich, et al., "Heterocyclic alpha-carbinolamines with the Isoquinuclidine skeleton. 3. Benzolsoquinuclidines", *Chemical Abstracts*, 97 (21), Abstract No. 182180s, (1982), 806.

Ramesh, D., et al., "Studies on Polycyclic Azaarenes. 2. Sythesis of Trans-3,4-dihydroxy-3,-dihydrobenz[c]acridine and trans-8,9-dihydroxy-8,9-dihydrobenz[c]acridine", *Chemical Abstracts*, 108, Abstract No. 37626, (1988), 2 pgs.

Ray, Jayanta K., et al., "A Facile and Convenient Method for the Synthesis of 8-methoxy-10,11-dihydronaphto[1,2-b]quinolines", *Chemical Abstracts*, 92, Abstract No. 76254, (1980), 30-31.

Safaryan, G. P., et al., "2-Benzopyrylium salts. 25, Reaction of 2-benzopyrylium salts with some nucleophiles", *Chemical Abstracts*, 96(17), Abstract No. 142656z, (1982), 739.

Schiess, P., et al., "Thermolytic ring opening of acyloxybenzocyclobutenes: an efficient route to 3-substituted isoquinolines", *Chemical Abstracts*, 104(19), Abstract No. 168332z, (1986), 639.

Sethi, Manohar L., "Enzyme Inihibition VI: Inhibition of Reverse Transcriptase Activity by Protoberberine Alkaloids and Structure-Activity Relationships", *Journal of Pharmaceutical Sciences*,72(5), (1983), 538-541.

Shcherbakova, I. V., et al., "2-Benzopyrilium salts. 35. Synthesis of the natural alkaloid dehydronorcoralydine and other substituted salts of dibenzo[a,g] quinolizine", *Chemical Abstracts*, 112 (19), Abstract No. 179554, (1990), 823.

Shelanski, H. A., "Acute and Chronic Toxicity Tests on Electrolytic Iron Powder", *Bulletin of the National Formulary Committee*, XVIII (5-6), (1950), 81-87.

Singh, S. K., et al., "Nitro and Amino Substitution in the D-Ring of 5-(2-Dimethylaminoethyl)-2,3-methylenedioxy-5H-dibenzo [c,h] [1,6] naphthyridine-6-ones: Effect on Topoisomerase-I Targeting Activity and Cytotoxicity", *Journal of Medicinal Chemistry*, 46(11), (2003), 2254-2257.

Singh, Malvinder P., et al., "Synthesis and Sequence-Specific DNA Binding of a Topoisomerase Inhibitory Analog of Hoechst 33258 Designed for Altered Base and Sequence Recognition", *Chem. Res. Toxicol.*, 5, (1992), pp. 597-607.

Sotomayor, N., et al., "Oxidation reactions of 2'-functionalized 3-aryltetrahydro-and 3,4-dlhydroisoquinolines", *Chemical Abstracts*, 124 (11), Abstract No. 145854, (1996), p. 1227.

Southard, G. L., et al., "Drug Delivery Devices", *USPATFULL Database*, No. 91:36238, RN No. 218-38-2, (Benzo[c]phenanthradine), from U.S. Patent 5,013,55., (1991), 2 pages.

Stermitz, Frank R., "Synthesis and Biological Activity of Some Antitumor Benzophenanthridinum Salts", *Journal of Medicinal Chemistry*, 18(7), (1975),708-713.

Studier, F. W., et al., "Use of T7 RNA polymerase to direct expression of cloned genes", *Methods in Enzymology*, 185, (1990), 80-89.

Sun, Qun, et al., "Structure activity of novel topoisomerase I Inhibitors related to Hoechst 33342", *Abstract 6—Proceedings of the American Association of Pharmaceutical Scientists Eastern Regional Meeting*, Hyatt Regency Hotel, New Brunswick, NJ, (Jun. 5-6,1995), p. 25.

Sun, Qun, et al., "Structure Activity of Topoisomerase I Poisons Related to Hoechst 33342", *Bioorganic & Medicinal Chemistry Letters*, 4 (24), (1994), pp. 2871-2876.

Sun, Qun, et al., "Structure-activity studies related to minor groove-binding ligands which inhibit mammalian DNA topoisomerase I", *Cancer Institute of New Jersey's First Annual Scientific Retreat, Abstract 2*, Princeton Marriott Forrestal Village, Princeton, NJ, (Jun. 7, 1994), p. 66.

Sun, Q., et al., "Synthesis and evaluation of terbenzimidazoles as topoisomerase I inhibitors",*Journal of Medicinal Chemistry*, 38(18), (1995), 3638-3644

Sun, Qun, et al., "Synthesis and Evaluation of Terbenzimidazoles as Topoisomerase I Inhibitors", *Chemical Abstracts*, vol. 123, No. 15, Abstract No. 198740r, (1995), 1241.

Sun, Qun, et al., "Synthesis and Pharmacological Evaluation of a Series of Novel DNA Topoisomerase I Inhibitors as Antitumor Agents", *Scientific Proceedings of 86th Annual Meeting of the American Association for Cancer Research, Abstract 3*, vol. 36, Toronto, Canada, (Mar. 1995).

Sun, Qun, et al., "Synthesis and pharmacological evaluation of a series of novel DNA topoisomerase I Inhibitors as antitumor agents", *Abstract 5—Proceedings of the 3rd Annual Scientific Retreat of the Cancer Institute of New Jersey*, Princeton Marriott Forrestal Village, Princeton, NJ,(1995), p. 27.

Sun, Qun, et al., "Synthesis of Benzimidazo[2,1-a]Isoquinolines and 5,6-Dihydrobenzimidazo[2,1-a]isoquinolines", *Syn. Lett., submitted*, Paper No. 7,(1995), 6 pages.

Tamura, H., et al., "Molecular cloning of a cDNA of a camptothecin-resistant human DNA topoisomerase I and identification of mutation sites", *Nucleic Acids Research*, 19 (1), (1991), pp. 69-75.

Tewey, K M., et al., "Adriamycin-induced DNA damage mediated by mammalian DNA topoisomerase II", *Science*, 226(4673), (1984), 466-8.

Vinogradov, A. E., et al., "Some properties of new DNA specific bisbenzimidazole fluorochromes without a piperazine ring", *Biotechnic & Histochemistry*, 68 (5), (1993), pp. 265-270.

Walterova, D., et al., "Isolation, Chemistry and Biology of Alkaloids from plants of Papaveraceae. Part XCV. Practical application of isotachophoresis in analysis of isoquinoline alkaloids", *Chemical Abstract*, vol. 104, No. 12, (1986), 454.

Wang, Li-Kai, et al., "Inhibition of Topoisomerase I Function by Coralyne and 5,6 -Dihydrocoralyne", *Chem. Res. Toxicol.*, 9, (1996), pp. 75-83.

Wang, Li-Kai, et al., "Inhibition of Topoisomerase I Function by Nitidine and Fagaronine", *Chem. Res. Toxicol.*, 6, (1993), pp. 813-818.

Wang, Huimin, et al., "Stimulation of topoisomerase II-mediated DNA damage via a mechanism involving protein thiolation", *Biochemistry*, 40(11), American Chemical Society,(2001),3316-3323.

Waters, W. A., et al., "Reactions of Free Benzyl Radicals with Benz[a]- and Benz[c]acridine", *Chemical Abstracts*, 54 (4), Abstract, col. 3424b, (1960).

Wilson, W. D., et al., "Coralyne. Intercalation with DNA as a Possible Mechanism of Antileukemic Action", *Journal of Medicinal Chemistry*, 19(10), Communications to the Editior, (1976), 1261-1263.

Yadagiri, Bathini, et al., "Convenient Routes to Substituted Benzimidazoles and Imidazolo[4,5-b]pyridines Using Nitrobenzene as Oxidant", *Synthetic Communications*, 20 (7), (1990), 955-963.

Yamamoto, Yutaka, et al., "Reaction of 6H-1, 3-oxazin-6-one with benzyne giving isoquinoline derivatives", *Chemical Abstracts*, 118(7), Abstract No. 059563u, (1993), 831.

Yamashita, Yoshinori, et al., "Induction of Mammalian DNA Topoisomerase I and II Mediated DNA Cleavage by Saintopin, a New Antitumor Agent from Fungus", *Biochemistry*, 30(24), (1991), 5838-5845.

Yamashita, Yoshinori , "Induction of Mammalian DNA Topoisomerase I Mediated DNA Cleavage by Antitumor Indolocarbazole Derivatives", *Biochemistry*, 31 (48), (1992), 12069-12075.

Zee-Cheng, K., et al., "Experimental Antileukemic Agents. Coralyne, Analogs, and Related Compounds", *Journal of Medicinal Chemistry*, 17(3), (1974), 347-351.

Zee-Cheng, K. Y., et al., "Practical Preparation of Coralyne Chloride", *Journal of Pharmaceutical Sciences*, 61 (6), (1972), 969-971.

Zee-Cheng, R. K., et al., "Tetramethoxydibenzoquinolizinium Salts, Preparation and Antileukemic Activity of Some Positional and Structural Isomers of Coralyne", *Journal of Medicinal Chemistry*, 19(7), (1976), 882-886.

* cited by examiner

SOLUBILIZED TOPOISOMERASE POISONS

CROSS REFERENCE TO RELATED APPLICATION

This application is a continuation of U.S. Ser. No. 10/846,834 filed on May 14, 2004, now U.S. Pat. No. 7,049,315, which is a continuation of International Patent Application PCT/US02/36901, filed Nov. 14, 2002 and published in English on May 22, 2003 as WO 03/041660 A2, which claimed priority under 35 U.S.C. 119(e) of U.S. Provisional Application No. 60/332,734, filed Nov. 14, 2001, which applications and publications are incorporated herein by reference.

BACKGROUND OF THE INVENTION

DNA-topoisomerases are enzymes which are present in the nuclei of cells where they catalyze the breaking and rejoining of DNA strands, which control the topological state of DNA. Recent studies also suggest that topoisomerases are also involved in regulating template supercoiling during RNA transcription. There are two major classes of mammalian topoisomerases. DNA-topoisomerase-I catalyzes changes in the topological state of duplex DNA by performing transient single-strand breakage-union cycles. In contrast, mammalian topoisomerase II alters the topology of DNA by causing a transient enzyme bridged double-strand break, followed by strand passing and resealing. Mammalian topoisomerase II has been further classified as Type II α and Type II β. The antitumor activity associated with agents which are topoisomerase poisons is associated with their ability to stabilize the enzyme-DNA cleavable complex. This drug-induced stabilization of the enzyme-DNA cleavable complex effectively converts the enzyme into a cellular poison.

Several antitumor agents in clinical use have potent activity as mammalian topoisomerase II poisons. These include adriamycin, actinomycin D, daunomycin, VP-16, and VM-26 (teniposide or epipodophyllotoxin). In contrast to the number of clinical and experimental drugs which act as topoisomerase II poisons, there are currently only a limited number of agents which have been identified as topoisomerase I poisons. Camptothecin and its structurally-related analogs are among the most extensively studied topoisomerase I poisons. Recently, bi- and terbenzimidazoles (Chen et al., *Cancer Res.* 1993, 53, 1332-1335; Sun et al., *J. Med. Chem.* 1995, 38, 3638-3644; Kim et al., *J. Med. Chem.* 1996, 39, 992-998), certain benzo[c]phenanthridine and protoberberine alkaloids and their synthetic analogs (Makhey et al., *Med. Chem. Res.* 1995, 5, 1-12; Janin et al., *J. Med. Chem.* 1975, 18, 708-713; Makhey et al., *Bioorg. & Med. Chem.* 1996, 4, 781-791), as well as the fungal metabolites, bulgarein (Fujii et al., *J. Biol. Chem.* 1993, 268, 13160-13165) and saintopin (Yamashita et al., *Biochemistry* 1991, 30, 5838-5845) and indolocarbazoles (Yamashita et al., *Biochemistry* 1992, 31, 12069-12075) have been identified as topoisomerase I poisons. Other topoisomerase poisons have been identified including certain benzo[i]phenanthridine and cinnoline compounds (see LaVoie et al., U.S. Pat. No. 6,140,328 (735.037WO1), and WO 01/32631(735.044WO1)). While these compounds are useful they are somewhat limited due to low solubility.

SUMMARY OF THE INVENTION

Applicant has discovered compounds with improved solubility properties which also have inhibitory activity against topoisomerase I and/or topoisomerase II. Accordingly, the invention provides a compound of the invention which is a compound of formula I:

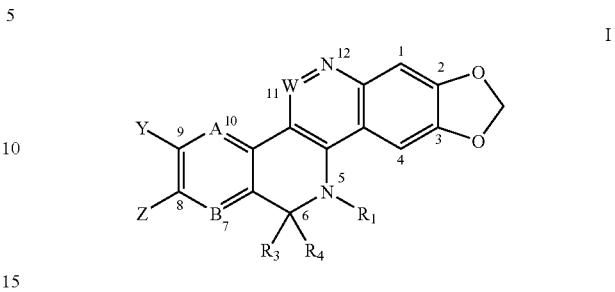

wherein:
A and B are independently N or CH;
W is N or CH;
$R_3$ and $R_4$ are each independently H, $(C_1\text{-}C_6)$alkyl, or substituted $(C_1\text{-}C_6)$alkyl, or $R_3$ and $R_4$ together are =O, =S, =NH or =N—$R_2$;
Y and Z are independently hydroxy, $(C_1\text{-}C_6)$alkoxy, substituted $(C_1\text{-}C_6)$alkoxy, $(C_1\text{-}C_6)$alkanoyloxy, substituted $(C_1\text{-}C_6)$alkanoyloxy, —O—P(=O)(OH)$_2$, or —O—C(=O)NR$_c$R$_d$; or Y and Z together with the ring carbon atoms to which they are attached form an alkylenedioxy ring with from 5 to 7 ring atoms;
$R_1$ is a —$(C_1\text{-}C_6)$alkyl substituted with one or more solubilizing groups $R_2$;
$R_2$ is $(C_1\text{-}C_6)$alkyl or substituted $(C_1\text{-}C_6)$alkyl; and
$R_c$ and $R_d$ are each independently $(C_1\text{-}C_6)$ alkyl or substituted $(C_1\text{-}C_6)$ alkyl; or $R_c$ and $R_d$ together with the nitrogen to which they are attached form a N'—{$(C_1\text{-}C_6)$ alkyl}piperazino, pyrrolidino, or piperidino ring, which ring can optionally be substituted with one or more aryl, heteroaryl, or heterocycle;
or a pharmaceutically acceptable salt thereof.

The invention also provides a pharmaceutical composition comprising a effective amount of a compound of the invention in combination with a pharmaceutically acceptable diluent or carrier.

The invention also provides a method for modulating topoisomerase activity in a mammal in need of such treatment comprising administering to the mammal, an amount of a compound of the invention effective to provide a topoisomerase modulating effect.

The invention also provides a method of inhibiting cancer cell growth, comprising administering to a mammal afflicted with cancer, an amount of a compound of the invention, effective to inhibit the growth of said cancer cells.

The invention also provides a method comprising inhibiting cancer cell growth by contacting said cancer cell in vitro or in vivo with an amount of a compound of the invention, effective to inhibit the growth of said cancer cell.

The invention also provides a compound of the invention for use in medical therapy, preferably for use in treating cancer, for example, solid tumors, as well as the use of a compound of the invention for the manufacture of a medicament useful for the treatment of cancer, for example, solid tumors.

The invention also provides processes and novel intermediates disclosed herein which are useful for preparing compounds of the invention. Some of the compounds of formula I are useful to prepare other compounds of formula I.

DETAILED DESCRIPTION

The following definitions are used, unless otherwise described.

"($C_1$-$C_6$)alkyl" denotes both straight and branched carbon chains with one or more, for example, 1, 2, 3, 4, 5, or 6, carbon atoms, but reference to an individual radical such as "propyl" embraces only the straight chain radical, a branched chain isomer such as "isopropyl" being specifically referred to.

"Substituted ($C_1$-$C_6$)alkyl" is an alkyl group of the formula ($C_1$-$C_6$)alkyl as defined above wherein one or more (e.g. 1 or 2) carbon atoms in the alkyl chain have been replaced with a heteroatom independently selected from —O—, —S— and NR— (where R is hydrogen or $C_1$-$C_6$alkyl) and/or wherein the alkyl group is substituted with from 1 to 5 substituents independently selected from cycloalkyl, substituted cycloalkyl, ($C_1$-$C_6$)alkoxycarbonyl (e.g. —CO$_2$Me), cyano, halo, hydroxy, oxo (=O), carboxy (COOH), aryloxy, heteroaryloxy, heterocyclooxy, nitro, and —NR$^a$R$^b$, wherein R$^a$ and R$^b$ may be the same or different and are chosen from hydrogen, alkyl, arylalkyl, heteroarylalkyl, heterocycloalkyl, cycloalkyl, substituted cycloalkyl, aryl, heteroaryl and heterocyclic. Substituted ($C_1$-$C_6$)alkyl groups are exemplified by, for example, groups such as hydroxymethyl, hydroxyethyl, hydroxypropyl, 2-aminoethyl, 3-aminopropyl, 2-methylaminoethyl, 3-dimethylaminopropyl, 2-carboxyethyl, hydroxylated alkyl amines, such as 2-hydroxyaminoethyl, and like groups. Preferred substituted ($C_1$-$C_6$)alkyl groups are ($C_1$-$C_6$)alkyl groups substituted with one or more substituents of the formula-NR$_a$R$_b$ where R$_a$ and R$_b$ together with the nitrogen to which they are attached form of nitrogen containing heterocyclic ring. Specific examples of such heterocyclic rings include piperazino, pyrrolidino, piperidino, morpholino, or thiomorpholino. Other preferred substituted ($C_1$-C6)alkyl groups are ($C_1$-C6)alkyl groups substituted with one or more carbon-linked oxygen containing heterocyclic rings. Specific examples of such oxygenated heterocyclic rings are, for example, tetrahydrofuranyl, tetrahydropyranyl, 1,4-dioxanyl, and like groups.

"($C_1$-$C_6$)alkoxy" refers to groups of the formula ($C_1$-$C_6$) alkyl-O—, where ($C_1$-$C_6$)alkyl is as defined herein. Preferred alkoxy groups include, by way of example, methoxy, ethoxy, propoxy, iso-propoxy, n-butoxy, tert-butoxy, sec-butoxy, n-pentoxy, n-hexoxy, 1,2-dimethylbutoxy, and like groups.

"Substituted ($C_1$-C6)alkoxy" refers to a substituted ($C_1$-$C_6$)alkyl-O—group wherein substituted ($C_1$-C6)alkyl is as defined above. Substituted ($C_1$-$C_6$)alkoxy is exemplified by groups such as O—CH$_2$CH$_2$—NR$_a$R$_b$, O—CH$_2$CH$_2$—CHR$_a$R$_b$, or O—CH$_2$—CHOH—CH$_2$—OH, and like groups. Preferred substituted ($C_1$-$C_6$)alkoxy groups are ($C_1$-$C_6$)alkyl substituted with one or more substituents of the formula-NR$_a$R$_b$ where R$_a$ and R$_b$ together with the nitrogen to which they are attached form of a heterocyclic ring. Specific examples of such heterocyclic rings include piperazino, pyrrolidino, piperidino, morpholino, or thiomorpholino. Other preferred substituted ($C_1$-$C_6$)alkoxy groups are ($C_1$-$C_6$) alkoxy groups substituted with one or more carbon-linked oxygen containing heterocyclic rings. Specific examples of preferred oxygenated heterocyclic ring substituents are, for example, tetrahydrofuranyl, tetrahydropyranyl, 1,4-dioxanyl, and like groups. Specific examples of such oxygenated heterocyclic rings are, for example, tetrahydrofuranyl, tetrahydropyranyl, 1,4-dioxanyl, and like groups.

"($C_1$-$C_6$)alkanoyloxy" includes, by way of example, formyloxy, acetoxy, propanoyloxy, iso-propanoyloxy, n-butanoyloxy, tert-butanoyloxy, sec-butanoyloxy, n-pentanoyloxy, n-hexanoyloxy, 1,2-dimethylbutanoyloxy, and like groups.

"Substituted ($C_1$-$C_6$)alkanoyloxy" refers to a ($C_1$-$C_6$)alkanoyloxy group wherein one or more (e.g. 1 or 2) carbon atoms in the alkyl chain have been replaced with a heteroatom independently selected from —O—, —S— and NR— (where R is hydrogen or $C_1$-$C_6$alkyl) and/or wherein the alkyl group is substituted with from 1 to 5 substituents independently selected from cycloalkyl, substituted cycloalkyl, ($C_1$-$C_6$)alkoxycarbonyl (e.g. —CO$_2$Me), cyano, halo, hydroxy, oxo (=O), carboxy (COOH), aryloxy, heteroaryloxy, heterocyclooxy, nitro, and —NR$^a$R$^b$, wherein R$^a$ and R$^b$ may be the same or different and are chosen from hydrogen, alkyl, arylalkyl, heteroarylalkyl, heterocycloalkyl, cycloalkyl, substituted cycloalkyl, aryl, heteroaryl and heterocyclic. Substituted ($C_1$-$C_6$)alkanoyloxy is exemplified by groups such as —O—C(=O)CH$_2$—NR$_a$R$_b$, and O—C(=O)—CHOH—CH$_2$—OH. Preferred substituted ($C_1$-$C_6$)alkanoyloxy groups are groups wherein the alkyl group is substituted with one or more nitrogen and oxygen containing heterocyclic rings such as piperazino, pyrrolidino, piperidino, morpholino, thiomorpholino, tetrahydrofuranyl, tetrahydropyranyl, 1,4-dioxanyl, and like groups.

Aryl denotes a phenyl radical or an ortho-fused bicyclic carbocyclic radical having about nine to ten ring atoms in which at least one ring is aromatic. Examples of aryl include phenyl, indenyl, and naphthyl.

Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, ($C_1$-$C_4$)alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto. Examples of heteroaryl include furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) and quinolyl (or its N-oxide).

The term "heterocycle" refers to a monovalent saturated or partially unsaturated cyclic non-aromatic group which contains at least one heteroatom, preferably 1 to 4 heteroatoms, selected from nitrogen (NR$_x$, wherein R$_x$ is hydrogen, alkyl, or a direct bond at the point of attachment of the heterocycle group), sulfur, phosphorus, and oxygen within at least one cyclic ring and which may be monocyclic or multi-cyclic. Such heterocycle groups preferably contain from 3 to 10 atoms. The point of attachment of the heterocycle group may be a carbon or nitrogen atom. This term also includes heterocycle groups fused to an aryl or heteroaryl group, provided the point of attachment is on a non-aromatic heteroatom-containing ring. Representative heterocycle groups include, by way of example, pyrrolidinyl, piperidinyl, piperazinyl, imidazolidinyl, morpholinyl, indolin-3-yl, 2-imidazolinyl, 1,2,3,4-tetrahydroisoquinolin-2-yl, quinuclidinyl and the like.

"Aryloxy" refers to a group of the formula aryl-O—, where aryl is as defined herein. Examples of aryloxy groups include, phenoxy and 1-naphthyloxy.

"Heteroaryloxy" refers to a group of the formula heteroaryl-O—, where heteroaryl is as defined herein. Examples of heteroaryloxy groups include, 3-piperidyloxy, 3-furyloxy, and 4-imidazoyloxy.

"Heterocyclooxy" refers to a group of the formula heterocycle-O—, where heterocycle is as defined herein. Examples of heterocyclooxy groups include, 4-morpholinooxy and 3-tetrahydrofuranyloxy.

"Arylalkyl" refers to a group of the formula aryl-($C_1$-$C_6$)alkyl-, where aryl and ($C_1$-$C_6$)alkyl are as defined herein.

"Heteroarylalkyl" refers to a group of the formula heteroaryl-($C_1$-$C_6$)alkyl-, where heteroaryl and ($C_1$-$C_6$)alkyl are as defined herein.

"Heterocycloalkyl" refers to a group of the formula heterocycle-($C_1$-$C_6$)alkyl-, where heterocycle and ($C_1$-$C_6$)alkyl are as defined herein.

"Solubilizing group(s) $R_z$" is a substituent that increases the water solubility of the compound of formula I compared to the corresponding compound lacking the R substituent. Examples of solubilizing groups include substituents independently selected from substituted ($C_1$-$C_6$)alkyl, ($C_1$-$C_6$)alkoxycarbonyl (e.g. —$CO_2$Me), cyano, halo, hydroxy, oxo (=O), carboxy (COOH), aryloxy, heteroaryloxy, heterocyclooxy, nitro, and —$NR_aR_b$, wherein $R_a$ and $R_b$ may be the same or different and are chosen from hydrogen, alkyl, arylalkyl, heteroarylalkyl, heterocycloalkyl, cycloalkyl, substituted cycloalkyl, aryl, heteroaryl and heterocyclic.

Preferred $R_1$ groups are exemplified by, for example, groups such as hydroxymethyl, hydroxyethyl, hydroxypropyl, 2-aminoethyl, 3-aminopropyl, 2-methylaminoethyl, 3-dimethylaminopropyl, 2-carboxyethyl, hydroxylated alkyl amines, such as 2-hydroxyaminoethyl, and like groups. Other preferred $R_1$ groups are ($C_1$-$C_6$)alkyl groups substituted with one or more substituents of the formula —$NR_aR_b$ where $R_a$ and $R_b$ together with the nitrogen to which they are attached form a nitrogen containing heterocyclic ring, or ($C_1$-$C_6$)alkyl groups substituted with one or more oxygen containing heterocyclic rings. Specific examples of such heterocyclic rings include piperazino, pyrrolidino, piperidino, morpholino, or thiomorpholino. Still other preferred $R_1$ groups are ($C_1$-$C_6$)alkyl groups substituted with one or more carbon-linked oxygen containing heterocyclic rings. Specific examples of such oxygenated heterocyclic rings are, for example, tetrahydrofuranyl, tetrahydropyranyl, 1,4-dioxanyl, and like groups.

Specific and preferred values listed below for radicals, substituents, and ranges, are for illustration only; they do not exclude other defined values or other values within defined ranges for the radicals and substituents.

Specifically, ($C_1$-$C_6$)alkyl can be methyl, ethyl, propyl, isopropyl, butyl, iso-butyl, sec-butyl, pentyl, 3-pentyl, or hexyl.

Specifically, ($C_1$-$C_6$)alkoxy can be methoxy, ethoxy, propoxy, isopropoxy, butoxy, iso-butoxy, sec-butoxy, pentoxy, 3-pentoxy, or hexoxy.

A specific value for A is CH.
Another specific value for A is N.
A specific value for B is N.
Another specific value for B is CH.
A specific value for W is N.
Another specific value for W is CH.
A specific value for Y is OH.
Another specific value for Y is ($C_1$-$C_6$)alkoxy.
Another specific value for Y is —$OCH_3$.
Another specific value for Y is substituted ($C_1$-$C_6$)alkoxy.
Another specific value for Y is —$OCH_2CH_2OH$.
Another specific value for Y is —$OCH_2CH_2OCH_2CH_3$.
Another specific value for Y is —O—$CH_2$—CHOH—$CH_2$—OH.
Another specific value for Y is —O—$CH_2CH_2$—$NR_aR_b$ wherein $R_a$ and $R_b$ are hydrogen or ($C_1$-$C_6$)alkyl.

Another specific value for Y is —O—$CH_2CH_2$—$NR_aR_b$ wherein $R_a$ and $R_b$ together with the nitrogen to which they are attached form a piperazino, pyrrolidino, piperidino, morpholino, or thiomorpholino ring.
Another specific value for Y is —O—C(=O)$CH_2$—$NR_aR_b$.
Another specific value for Y is —O—C(=O)—CHOH—$CH_2$—OH.
Another specific value for Y is ($C_1$-$C_6$)alkyl substituted with one or more tetrahydrofuranyl, tetrahydropyranyl, or 1,4-dioxanyl rings.
Another specific value for Y is —O—C(=O)$CH_2$—$NR_aR_b$.
A specific value for Z is OH.
Another specific value for Z is ($C_1$-$C_6$)alkoxy.
Another specific value for Z is $OCH_3$.
Another specific value for Z is substituted ($C_1$-$C_6$)alkoxy.
Another specific value for Z is —$OCH_2CH_2OH$.
Another specific value for Z is —$OCH_2CH_2OCH_2CH_3$.
Another specific value for Z is —O—$CH_2$—CHOH—$CH_2$—OH.
Another specific value for Z is —O—$CH_2CH_2$—$NR_aR_b$ wherein $R_a$ and $R_b$ are hydrogen or ($C_1$-$C_6$)alkyl.
Another specific value for Z is —O—$CH_2CH_2$—$NR_aR_b$ wherein $R_a$ and $R_b$ together with the nitrogen to which they are attached form a piperazino, pyrrolidino, piperidino, morpholino, or thiomorpholino ring.
Another specific value for Z is —O—C(=O)—CHOH—$CH_2$—OH.
Another specific value for Z is ($C_1$-$C_6$)alkyl substituted with one or more tetrahydrofuranyl, tetrahydropyranyl, or 1,4-dioxanyl rings.
Another specific value for Z is —O—C(=O)$CH_2$—$NR_aR_b$.
A specific value for $R_3$ and $R_4$ is H.
Another specific value for $R_3$ and $R_4$ together is =O.
Another specific value for $R_3$ and $R_4$ together is =S.
Another specific value for $R_3$ and $R_4$ together is =NH.
Another specific value for $R_3$ and $R_4$ together is =N—$R_2$.
Another specific value for $R_3$ and $R_4$ together is =N—$R_2$ where $R_2$ is ($C_1$-$C_6$)alkyl.
Another specific value for $R_3$ and $R_4$ together is =N—$R_2$ where $R_2$ is substituted ($C_1$-$C_6$)alkyl.
Another specific value for $R_3$ is H and $R_4$ is ($C_1$-$C_6$)alkyl.
Another specific value for $R_3$ is H and $R_4$ is substituted ($C_1$-$C_6$)alkyl.
Another specific value for $R_3$ is ($C_1$-$C_6$)alkyl and $R_4$ is substituted ($C_1$-$C_6$)alkyl.
Another specific value for $R_3$ and $R_4$ is substituted ($C_1$-$C_6$)alkyl
A specific value for $R_1$ is 2-hydroxyethyl.
Another specific value for $R_1$ is 2-aminoethyl.
Another specific value for $R_1$ is 2-(N,N'-dimethylamino)ethyl.
Another specific value for $R_1$ is 2-(N,N'-diethylamino)ethyl.
Another specific value for $R_1$ is 2-(N,N'-diethanolamino)ethyl of the formula —$CH_2$—$CH_2$—N(—$CH_2$—$CH_2$—OH)$_2$.
Another specific value for $R_1$ or $R_2$ is a ($C_1$-$C_6$)alkyl substituted with one or more hydroxy, mercapto, carboxy, amino, piperazinyl, pyrrolidinyl, piperidinyl, morpholinyl, thiomorpholinyl, tetrahydrofuranyl, tetrahydropyranyl, or 1,4-dioxanyl groups.
Another specific value for $R_1$ or $R_2$ is a ($C_1$-$C_6$)alkyl with from 2 to 4 carbon atoms and substituted with one to two groups selected from hydroxy, mercapto, carboxy, amino, piperazinyl, pyrrolidinyl, piperidinyl, morpholinyl, thiomorpholinyl, tetrahydrofuranyl, tetrahydropyranyl, or 1,4-dioxanyl.

Another specific value for $R_1$ or $R_2$ is —$CH_2CH_2$—$NR_aR_b$ wherein $R_a$ and $R_b$ are hydrogen or $(C_1$-$C_6)$alkyl.

Another specific value for $R_1$ or $R_2$ is —$CH_2CH_2$—$NR_aR_b$ wherein $R_a$ and $R_b$ together with the nitrogen to which they are attached form a piperazino, pyrrolidino, piperidino, morpholino, or thiomorpholino ring.

A preferred compound of formula (I) is the compound 11,12-dihydro-2,3-dimethoxy-8,9-methylenedioxy-11-[2-(dimethylamino)ethyl]-5,6,11-triazachrysen-12-one, or a pharmaceutically acceptable salt thereof.

A specific compound of formula I is a compound of formula II:

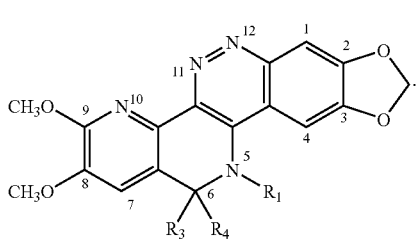

II

Another specific compound of formula I is a compound of formula III:

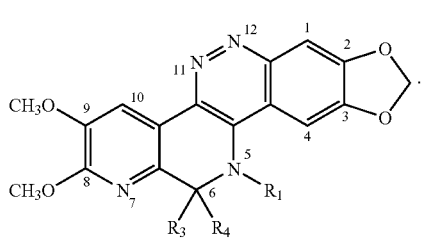

III

Another specific compound of formula I is a compound of formula IV:

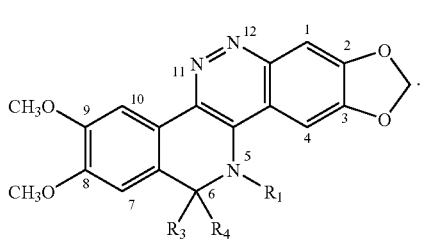

IV

Another specific compound of formula I is a compound of formula V:

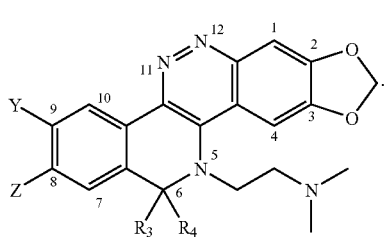

V

A specific compound of formula I is a compound of formula VI:

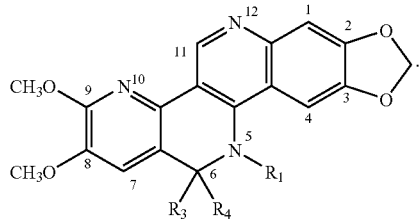

VI

Another specific compound of formula I is a compound of formula VII:

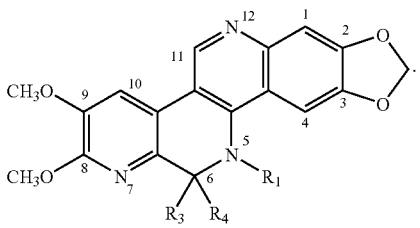

VII

Another specific compound of formula I is a compound of formula VIII:

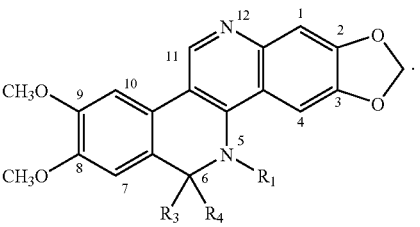

VIII

Another specific compound of formula I is a compound of formula IX:

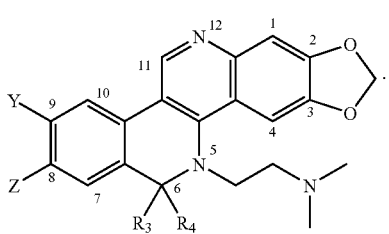

IX

Another specific compound of formula I is any of the above compounds of formulas II-IX as their pharmaceutically acceptable salts.

Certain compounds of formula (I) can function as prodrugs for other compounds of formula (I). For example, a compound of formula (I) wherein Y and/or Z is —O—P(=O)(OH)$_2$, or —O—C(=O)NR$_c$R$_d$; can function as a prodrug for a corresponding compound of formula (I) wherein Y and or Z is hydroxy. Accordingly, a specific sub set of compounds of formula (I) are compounds wherein Y and/or Z is —O—P(=O)(OH)$_2$, or —O—C(=O)NR$_c$R$_d$. A particularly preferred compound is a compound of formula (I) wherein Y and/or Z is —O—P(=O)(OH)$_2$. Another preferred compound is a compound of formula (1) wherein Y and/or Z is —O—C(=O)NR$_c$R$_d$, wherein R$_c$ and/or R$_d$ is (C$_1$-C$_6$)alkyl substituted with one or more —NR$_e$R$_f$ wherein R$_e$ and R$_f$ are each independently (C$_1$-C$_6$)alkyl. Another preferred compound is a compound of formula (I) wherein Y and/or Z is —O—C(=O)NR$_c$R$_d$, wherein R$_c$ and R$_d$ together with the nitrogen to which they are attached form a N'—{(C$_1$-C$_6$)alkyl}piperazino, pyrrolidino, or piperidino ring. A more preferred compound is a compound of formula (I) wherein Y and/or Z is —O—C(=O)NR$_c$R$_d$, wherein R$_c$ and R$_d$ together with the nitrogen to which they are attached form a piperidino ring, which ring is optionally substituted with an N-linked heterocycle (e.g. piperidino) ring.

The present invention provides compounds and intermediate compounds of formula I and a method of making compounds of formula I and intermediate compounds of formula I wherein R$_1$ is —CH$_2$—OH and like 1-hydroxy substituted (C$_1$-C$_6$)alkyl groups, or the corresponding alkanoyloxy ester, phosphoric acid ester, or phosphate ester comprising reacting the compound of formula I where R$_1$ is H with a suitable hydroxy producing compound, for example a carbonyl compound, such as an aldehyde, to form a compound where R$_1$ is —CH$_2$—OH or like 1-hydroxy substituted (C$_1$-C$_6$)alkyl groups. The corresponding alkanoyloxy ester, phosphoric acid ester or phosphate ester compounds can be prepared by reacting the resulting compound where R$_1$ is —CH$_2$—OH or like 1-hydroxy substituted (C$_1$-C$_6$)alkyl groups with a suitable ester forming reagent, such as an acyl halide, phosphoric acid ester, or phosphoryl halide compound. The above intermediate compounds can also function as prodrugs for other compounds of formula (I). It is understood by one skilled in the art that the groups here R$_1$ is —CH$_2$—OH or like 1-hydroxy substituted (C$_1$-C$_6$)alkyl groups can be stabilized or preserved with known protecting groups, such as carboxylate esters, phosphates, and like groups. See for example, Krogsgaard-Larsen P and Bundgaard A (eds), "*A Textbook Of Drug Design and Development*," 2nd ed., Harwood, 1996.

A compound of formula I can be prepared by subjecting a corresponding intermediate of formula A to suitable cyclization conditions; for example, by treatment with palladium acetate and triphenyl phosphine, as illustrated in Scheme 1 below. A compound of formula I can also be prepared by subjecting a corresponding intermediate of formula B to conditions suitable for the formation of the tetracyclic ring system; for example by treatment with a suitable tin reagent, as illustrated in Scheme 2 below. Compounds of the present invention include intermediates of formulas A and B.

Scheme 1

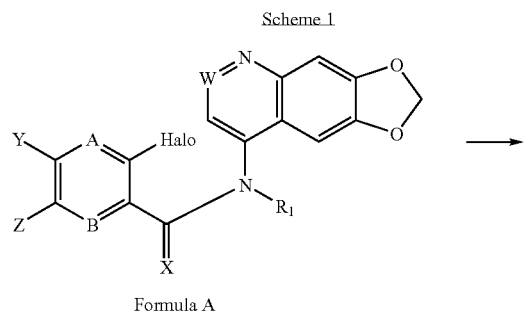

Formula A

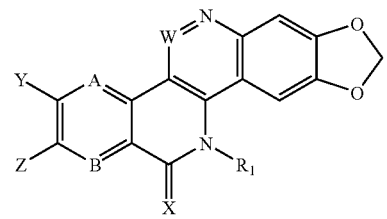

Formula I

Scheme 2

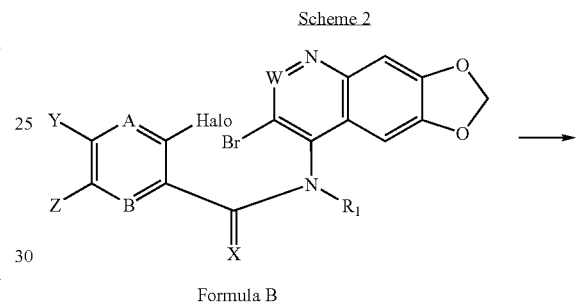

Formula B

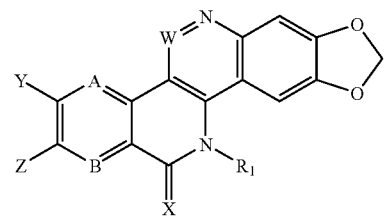

Formula I

Other conditions suitable for formation of the ring system from intermediates of formula A and formula B are well known to the art. For example, see Feiser and Feiser, "Reagents for Organic Synthesis", Vol. 1, 1967; March, J. "Advanced Organic Chemistry", John Wiley & Sons, 4th ed., 1992; House, H. O., "Modern Synthetic Reactions", 2d ed., W. A. Benjamin, New York, 1972; and Larock, R. C., *Comprehensive Organic Transformations,* 2nd ed., 1999, Wiley-VCH Publishers, New York.

An intermediate of formula A can be prepared from readily available starting materials using procedures that are known in the art, or can be prepared using procedures illustrated below.

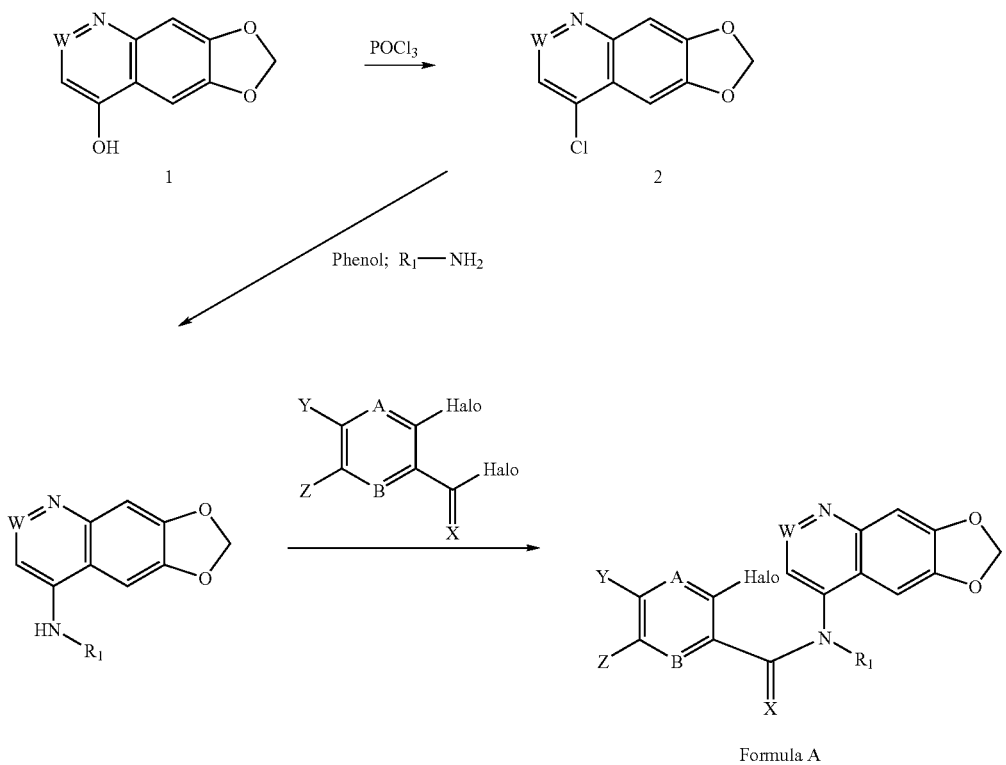

Chlorination of Compound 1 yields chloro-compound 2, which can be converted to the corresponding amine by formation of the corresponding phenoxy intermediate and subsequent reaction with an appropriate amine. The resulting amine can be acylated with the appropriately substituted acyl-chloride to provide the intermediate of formula A.

Similarly, an intermediate of formula B can be prepared from readily available starting materials using procedures that are known in the art, or can be prepared using procedures illustrated below.

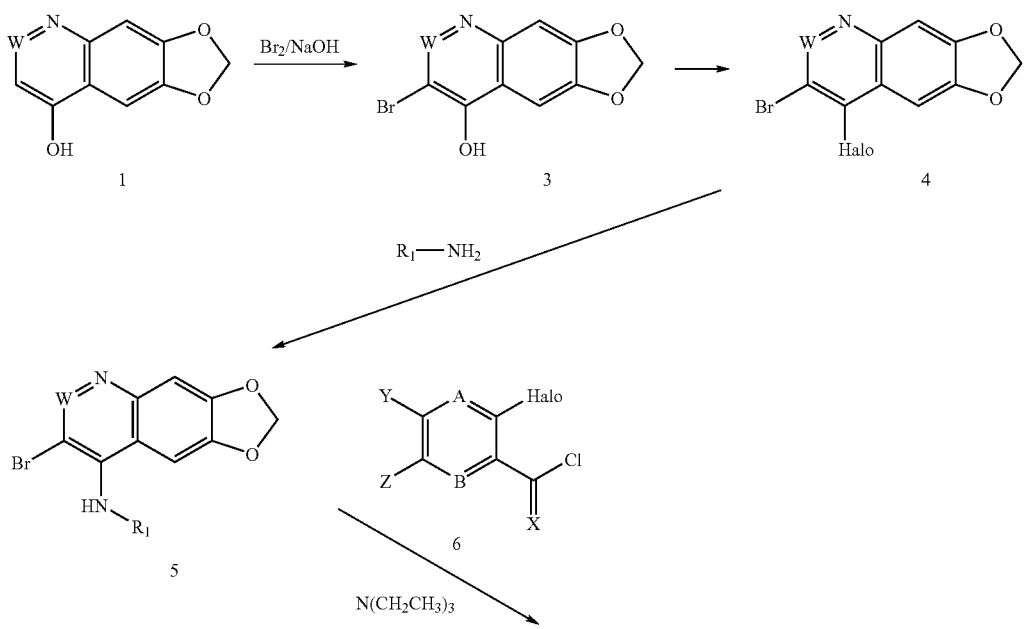

-continued

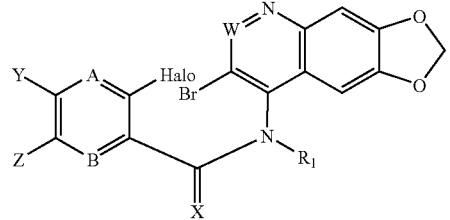

Formula B

Bromination of compound 1 provides compound 3, which can be converted to halo-compound 4 using procedures known in the art. Reaction with a suitable amine or ammonium salt provides amino compound 5, which can be converted to an intermediate of formula B by treatment with a suitable acid chloride 6.

An alternative route to the formation of 5,6-dihydro derivatives of formula I involves either reduction of the lactam or desulfurization of the thioamide as illustrated by the following. Additionally, one can modify compounds of formula I to provide other related compounds of formula I as illustrated below.

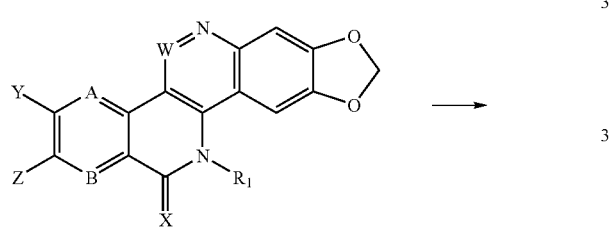

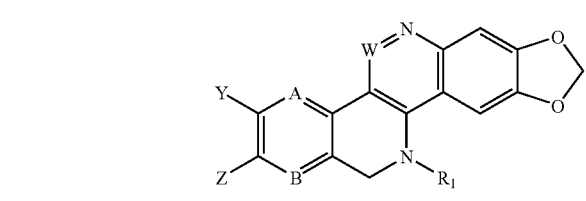

Where X = O or S

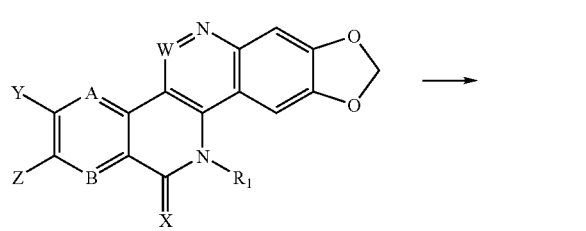

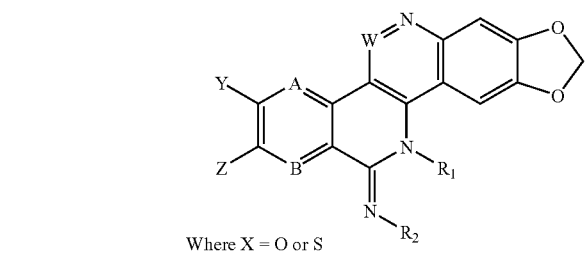

Where X = O or S

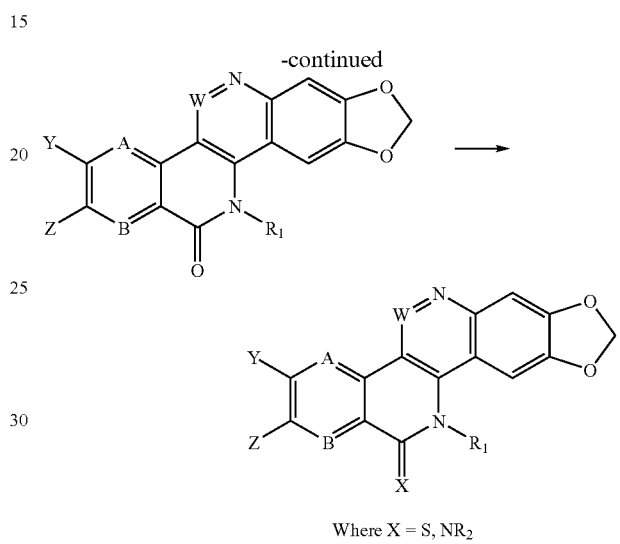

Where X = S, NR$_2$

The starting materials employed in the synthetic methods described herein are commercially available, have been reported in the scientific literature, or can be prepared from readily available starting materials using procedures known in the field. It may be desirable to optionally use a protecting group during all or portions of the above described synthetic procedures. Such protecting groups and methods for their introduction and removal are well known in the art. See Greene, T. W.; Wutz, P. G. M. "Protecting Groups In Organic Synthesis" second edition, 1991, New York, John Wiley & Sons, Inc.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine topoisomerase inhibition activity or cytotoxic activity using the standard tests described herein, or using other similar tests which are well known in the art. Compounds of the present invention can contain chiral centers, for example, at ring atom position 6 in formula I when R$_3$ and R$_4$ are different. Compounds of the present invention can also contain chiral centers, for example, in any of the substituents Y, Z, $R_1$, $R_2$ when $R_3$ and $R_4$ together are =N—$R_2$, and $R_3$ or $R_4$.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal, for example, sodium, potassium or lithium, or alkaline earth metal, for example calcium, salts of carboxylic acids can also be made.

The compounds of formula I can be formulated as pharmaceutical compositions and administered to a mammalian host, such as a human patient in a variety of forms adapted to the chosen route of administration, that is, orally or parenterally, by intravenous, intramuscular, topical or subcutaneous routes.

Thus, the present compounds may be systemically administered, for example, orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound may conveniently be administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The ability of a compound of the invention to effect topoisomerase I or II mediated DNA cleavage can be determined using pharmacological models that are well known to the art, for example, using a model like Test A described below.

Test A. Topoisomerase I-Mediated DNA Cleavage Assay

Human topoisomerase I was expressed in *E. Coli* and isolated as a recombinant fusion protein using a T7 expression system as described previously, see Makhey, D. et al., *Bioorg. Med. Chem.*, 2000, 8, 1-11. DNA topoisomerase I was purified from calf thymus gland as reported previously, see Maniatis, T., et al., J. Molecular Cloning, a Laboratory Manual, Cold Spring Harbor Laboratory, Cold Spring Harbor, N.Y., 149-185). Plasmid YepG was also purified by the alkali lysis method followed by phenol deproteination and CsCl/ethidium isopycnic centrifugation method as described, see Maniatis, T.; Fritsch, E. F.; Sambrook, *J. Molecular Cloning, a Laboratory Manual*; Cold Spring Harbor Laboratory: Cold Spring Harbor, N.Y. 1982; pp 149-185. The end-labeling of the plasmid was accomplished by digestion with a restriction enzyme followed by end-filling with Klenow polymerase as previously described, see Liu, L. F.; Rowe, T. C.; Yang, L.; Tewey, K. M.; Chen, G. L., *J. Biol. Chem.* 1983, 258, 15365. Cleavage assays were performed as previously reported, see B. Gatto et al. *Cancer Res.*, 1996, 56, 2795-2800. The drug and the DNA in presence of topoisomerase I was incubated for 30 minutes at 37° C. After development of the gels, typically 24-hour exposure was used to obtain autoradiograms outlining the extent of DNA fragmentation. Topoisomerase I-mediated DNA cleavage values are reported as REC, Relative Effective Concentration, i.e. concentrations relative to 2,3-dimethoxy-8,9-methylenedioxybenzo[i] phenanthridine, whose value is arbitrarily assumed as 1.0, that are able to produce the same cleavage on the plasmid DNA in the presence of human topoisomerase I. Relative potency was based upon the relative amount of drug needed to induce approximately 10% DNA fragmentation. Assays are performed under the direction of Dr. L. F. Liu, Department of Pharmacology, The University of Medicine and Dentistry of New Jersey, Robert Wood Johnson Medical School, Piscataway, N.J.

A similar assay can be used to evaluate the ability of a compound of the invention to effect topoisomerase II mediated DNA cleavage, by replacing the human topoisomerase I used in Test A with a suitable topoisomerase II.

Camptothecin is recognized as being among the most potent topoisomerase I inhibitors. Compound 5 has similar potency as a topoisomerase I inhibitor to Irinotecan and Topotecan, both of which are in clinical use, as well as Camptothecin in the cleavable complex assay detailed herein.

TABLE 1

| Compound | RPMI 8402 [µM] IC$_{50}$ values | CPT-K5 |
|---|---|---|
| 5 | 0.003 | 1.2 |
| Camptothecin | 0.002 | 4.5 |
| Irinotecan | 0.57 | >100 |
| Topotecan | 0.005 | >10 |

The data in Table 1 demonstrate that a representative compound of the present invention can function as cytotoxic agents against tumor cell lines.

The cytotoxic effects of a compound of the invention can be determined using pharmacological models that are well known to the art, for example, using a model like Test B described below.

Test B. Inhibition of Cell Growth: MTT-Microtiter Plate Tetrazolinium Cytotoxicity Assay (RPMI 8402, CPT-K5, U937, U937/CR Cells)

The cytotoxicity is determined using the MTT-microtiter plate tetrazolinium cytotoxicity assay (MTA), see Chen A. Y. et al. *Cancer Res.* 1993, 53, 1332; Mosmann, T. J., *J. Immunol. Methods* 1983, 65, 55; and Carmichael, J. et al. *Cancer Res.* 1987, 47, 936. The human lymphoblast RPMI 8402 and its camptothecin-resistant variant cell line, CPT-K5 were provided by Dr. Toshiwo Andoh (Anchi Cancer Research Institute, Nagoya, Japan), see Andoh, T.; Okada, K, *Adv. in Pharmacology* 1994, 29B, 93. Human U-937 myeloid leukemia cells and U-937/CR cells were described by Rubin et al., *J. Biol. Chem.*, 1994, 269, 2433-2439. The cytotoxicity assay is performed by using 96-well microtiter plates using 2000 cells/well, in 200 mL of growth medium. Cells are grown in suspension at 37° C. in 5% $CO_2$ and maintained by regular passage in RPMI medium supplemented with 10% heat-inactivated fetal bovine serum, L-glutamine (2 mM), penicillin (100 U/mL), and streptomycin (0.1 mg/mL). For determination of IC$_{50}$, cells are exposed continuously for 3-4 days to varying concentrations of drug, and MTT assays were performed at the end of the fourth day. Each assay is performed with a control that did not contain any drug. All assays are performed at least twice in 6 replicate wells. All assays are performed under the direction of Dr. L. F. Liu, Department of Pharmacology, The University of Medicine and Dentistry of New Jersey, Robert Wood Johnson Medical School, Piscataway, N.J.

Topoisomerase inhibitors are also known to possess antibacterial, antifungal, antipsoritic (psoriasis), antiprotozoal, antihelmetic, and antiviral activity. Accordingly, the topoisomerase inhibitors of the invention may also be useful as antibacterial, antifungal, antipsoritic (psoriasis), antiprotozoal, antihelmetic, or antiviral agents. In particular, compounds of the invention that demonstrate little or no activity as mammalian topoisomerase I poisons, because of the possibility of similar molecular mechanism of action, could be highly active and selective antibacterial, antifungal, antipsoritic (psoriasis), antiprotozoal, antihelmetic, or antiviral agents. Thus, certain compounds of the invention may be particularly useful as systemic antibacterial, antifungal, antipsoritic (psoriasis), antiprotozoal, antihelmetic, or antiviral agents in mammals. The invention also provides the use of a compound of the invention for the manufacture of a medicament useful for producing an antibacterial, antifungal, antipsoritic (psoriasis), antiprotozoal, antihelmetic, or antiviral effect in a mammal.

As used herein, the term "solid mammalian tumors" include cancers of the head and neck, lung, mesothelioma, mediastinum, esophagus, stomach, pancreas, hepatobiliary system, small intestine, colon, rectum, anus, kidney, ureter, bladder, prostate, urethra, penis, testis, gynecological organs, ovarian, breast, endocrine system, skin central nervous system; sarcomas of the soft tissue and bone; and melanoma of cutaneous and intraocular origin. The term "hematological malignancies" includes childhood leukemia and lymphomas, Hodgkin's disease, lymphomas of lymphocytic and cutaneous origin, acute and chronic leukemia, plasma cell neoplasm and cancers associated with AIDS. The preferred mammalian species for treatment are humans and domesticated animals.

The invention will now be illustrated by the following non-limiting Examples, wherein unless otherwise stated: melting points were determined with a Thomas-Hoover Unimelt capillary melting point apparatus; column chromatography refers to flash chromatography conducted on SiliTech 32-63 m, (ICN Biomedicals, Eschwegge, Ger.) using the solvent systems indicated; radial chromatography refers to the use of a Model 8924 chromatotron (Harrison Research, CA); infrared spectral data (IR) were obtained on a Perkin-Elmer 1600 Fourier transform spectrophotometer and are reported in $cm^{-1}$; proton ($^1$H NMR) and carbon ($^{13}$C NMR) nuclear magnetic resonance were recorded on a Varian Gemini-200 Fourier Transform spectrometer; NMR spectra (200 MHz $^1$H and 50 MHz $^{13}$C) were recorded in the deuterated solvent indicated with chemical shifts reported in units downfield from tetramethylsilane (TMS); coupling constants are reported in hertz (Hz); mass spectra were obtained from Washington University Resource for Biomedical and Bioorganic Mass Spectrometry within the Department of Chemistry at Washington University, St. Louis, Mo.; combustion analyses were performed by Atlantic Microlabs, Inc., Norcross, Ga., and were within 0.4% of the theoretical value.

Specific compounds of the present invention can be prepared in accordance with the following scheme using, for example, the reactions and reagents illustrated.

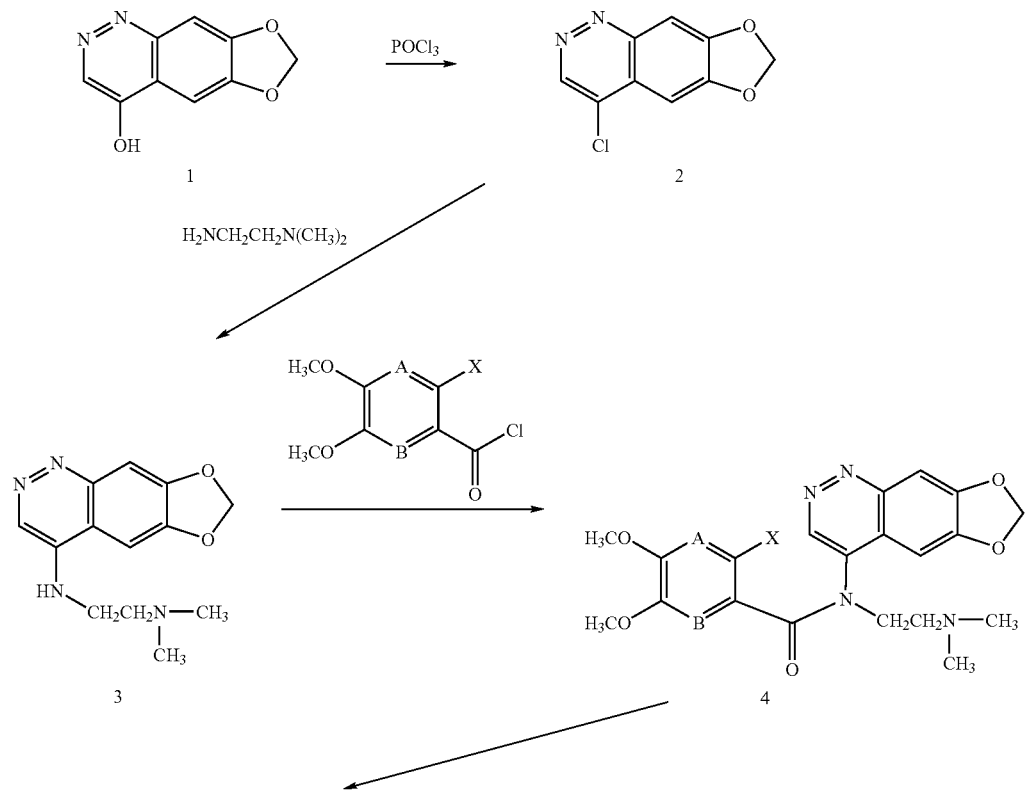

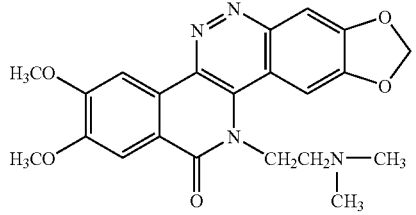

5

EXAMPLE 1

11,12-dihydro-2,3-dimethoxy-8,9-methylenedioxy-11-[2-(dimethylamino)ethyl]-5,6,11-triazachrysen-12-one (5). A mixture of 4-N-(2-Dimethylaminoethyl)-N-(2-bromo-4,5-dimethoxybenzoyl)amine-6,7-methylenedioxycinnoline (4, 220 mg, 0.40 mmol), Pd(OAc)$_2$ (18.0 mg, 0.08 mmol), P(o-tolyl)$_3$ (48.8 mg, 0.16 mmol), and silver carbonate (225 mg, 0.80 mmol) were heated to reflux in DMF (12 mL) and stirred under nitrogen for 75 minutes. The reaction mixture was cooled to room temperature, diluted with chloroform and filtered though a bed of celite. The solvent was removed under reduced pressure and the resulting residue was chromatographed on silica gel using 95:5 chloroform:methanol to give the title compound (60 mg) in 36% yield; $^1$H NMR (CDCl$_3$) δ 2.42(s, 6H), 3.04(t, 2H, J=7.2 Hz), 4.08(s, 3H), 4.17(s, 3H), 4.64(t, 2H, J=7.2 Hz), 6.25(s, 2H), 7.81(s, 1H), 7.84(s, 1H), 8.07(s, 1H), 8.65(s, 1H); $^{13}$C NMR (CDCl$_3$) δ 45.9, 47.4, 56.4, 56.7, 57.7, 99.4, 102.8, 104.3, 106.6, 107.9, 113.7, 119.6, 129.1, 131.0, 134.4, 149.4, 150.2, 151.5, 154.4, 163.1; HRMS calcd. for C$_{22}$H$_{22}$O$_5$N$_4$H: 423.1668; found 423.1653.

The intermediate 4-N-(2-Dimethylaminoethyl)-N-(2-bromo-4,5-dimethoxybenzoyl)amine-6,7-methylenedioxycinnoline (4) was prepared as follows:

a. 4-N-(2-Dimethylaminoethyl)-N-(2-bromo-4,5-dimethoxybenzoyl)amine-6,7-methylenedioxycinnoline (4). A 2.0M solution of oxalyl chloride in methylene chloride (5 mL, 10.0 mmol) was added to a solution of 2-iodo-4,5-dimethoxybenzoic acid (1.50 g, 4.8 mmol) in anhydrous methylene chloride (45 mL) and the stirred mixture was refluxed for 2 hours. The mixture was then concentrated to dryness under reduced pressure. To this residue was added a solution of N-(2-Dimethylaminoethyl)-4-amino-6,7-methylenedioxycinnoline (3, 1.0 g, 3.84 mmol), and triethylamine (760 mg 7.52 mmol) in methylene chloride (60 mL) and the resulting mixture was stirred at reflux under nitrogen for 4 hours, then cooled to room temperature; stirring was continued overnight. The reaction mix was washed with a saturated solution of sodium bicarbonate (3×40 mL), dried (anhydrous MgSO$_4$), and concentrated in vacuo. The crude material was chromatographed over silica using 90:10 chloroform:methanol to give compound 4 (1.59 g), in 75% yield; $^1$H NMR (CDCl$_3$) δ 2.27(s, 6H), 2.53(m, 2H), 3.43(s, 3H), 3.75(s, 3H), 3.97(m, 1H), 4.44(m, 1H), 6.24(s, 1H), 6.25(s, 1H), 6.43(s, 1H), 7.02(s, 1H), 7.43(s, 1H), 7.68(s, 1H), 9.18(s, 1H); $^{13}$C NMR (CDCl$_3$) δ 45.5, 47.1, 55.7, 56.1, 56.7, 82.8, 96.7, 102.9, 105.4, 110.6, 121.9, 123.2, 133.1, 136.0, 144.8, 148.2, 149.9, 150.9, 151.7, 152.4, 169.8; HRMS calcd for C$_{22}$H$_{23}$O$_5$N$_4$IH: 551.0791; found 551.0795.

b. N-(2-Dimethylaminoethyl)-4-amino-6,7-methylenedioxycinnoline (3). 4-Chloro-6,7-methylenedioxycinnoline (350 mg, 1.7 mmol) and copper powder (100 mg, 1.6 mmol) in N,N-dimethylethylenediamine (3.75 g, 42.6 mmol) were stirred at 105° C. under nitrogen for 3 hours. Excess N,N-dimethylethylenediamine was removed by rotoevaporation, and the residue was dissolved in chloroform (50 mL), and washed with water (3×30 mL), dried (anhydrous MgSO$_4$), and concentrated in vacuo to give compound 3 (324 mg) in 74% yield; $^1$H NMR (CDCl$_3$) δ 2.33 (s, 6H), 2.70 (t, 2H), 3.38 (dt, 2H), 6.15 (s, 2H), 7.03 (s, 1H), 7.56 (s, 1H), 8.53 (s, 1H); $^{13}$C NMR (CDCl$_3$) δ 39.5, 45.1, 57.0, 94.7, 102.1, 105.3, 112.7, 128.8, 139.8, 147.8, 149.5, 150.7; HRMS calcd for C$_{13}$H$_{16}$O$_2$N$_4$: 260.1273; found 260.1267.

c. 4-Chloro-6,7-methylenedioxycinnoline (2). 4-Hydroxy-6,7-methylenedioxycinnoline (1, 1.0 g, 5.3 mmol) was added in small portions to a stirred mixture of phosphorus pentachloride (1.4 g, 6.7 mmol) and phosphorus oxychloride (4 mL, 6.6 mmol) at room temperature. The reaction flask was heated to 80° C. for 1 hour, then cooled to room temperature and poured onto 50 g of crushed ice. After neutralization of the solution with solid sodium acetate the precipitate was removed by filtration and recrystallized from ethanol to give 800 mg of 4-chloro-6,7-methylenedioxycinnoline, compound 2, in 73% yield; $^1$H NMR (CDCl$_3$) δ 6.25 (s, 2H), 7.39 (s, 1H), 7.73 (s, 1H), 9.14 (s, 1H); $^{13}$C NMR (CDCl$_3$) δ 97.8, 102.9, 105.1, 124.2, 133.4, 144.0, 150.0, 152.3, 152.7; HRMS calcd for C$_9$H$_5$O$_2$N$_2$Cl: 208.0040; found 208.0042.

d. 4-Hydroxy-6,7-methylenedioxycinnoline (1). 6'-Amino-3',4'-(methylenedioxy)acetophenone (2.4 g, 13.4 mmol) in concentrated hydrochloric acid (92 mL) and water (13 mL) was cooled to −5° C. and a diazotized by the dropwise addition of a solution of sodium nitrite (0.925 g, 13.4 mmol) in water (4 mL). After stirring for an additional hour at −5° C. the mixture was transferred to a bath preheated at 75° C. and left to stir at this temperature overnight. The reaction mixture was cooled to 5° C. to complete crystallization of the product in the form of its hydrochloride salt. This material was filtered and then added to 10% aqueous NaOH (100 mL) to generate the free base, which was again filtered and dried under vacuum to yield 2.37 g of the hydroxycinnoline, compound 1, in 93% yield; $^1$H NMR (d$_6$-DMSO) δ 6.21(s, 2H), 6.97 (s, 1H), 7.30 (s, 1H), 7.63 (s, 1H); $^{13}$C NMR (d$_6$-DMSO) δ 94.9, 100.29, 103.3, 120.1, 139.7, 139.9, 147.4, 153.5, 169.4; HRMS calcd for C$_9$H$_6$O$_3$N$_2$: 190.0378; found 190.0372.

EXAMPLES 2-6

The representative compounds of the invention at Examples 2-6 were prepared using the following general procedure from the intermediates prepared in the correspondingly numbered sub-parts a below.

A mixture of the requisite 4-amino-6,7-methylenedioxycinnoline o-iodobenzamide derivative (1.0 mmol equiv.), Pd(OAc)$_2$ (0.2 mmol equiv.), P(o-tolyl)$_3$ (0.4 mmol equiv.), and Ag$_2$CO$_3$ (2.0 mmol equiv) was heated to reflux in DMF (30 mL per mmol equiv.) with stirring. The reaction mixture was allowed to cool to room temperature, diluted with CHCl$_3$, and filtered through Celite. The sicciate was extensively washed with 10% CH$_3$OH in CHCl$_3$. The filtrate was concentrated in vacuo and the residue chromatographed on silica gel using chloroform:methanol to provide the title compound.

EXAMPLE 2

2,3-Dimethoxy-8,9-methylenedioxy-11-[(2-diethylamino)ethyl]-11H-5,6,11-triaza-chrysen-12-one: Prepared from N-(6,7-Methylenedioxycinnolin-4-yl)-N—(N,N-diethylaminoethyl)-2-iodo-4,5-dimethoxybenzamide (578 mg, 1.0 mmol); (18% yield); reaction time 25 min; mp 245-247° C.(dec.); IR (CHCl$_3$) 1652; $^1$H NMR (CDCl$_3$) δ 1.08 (t, 6H, J=7.0), 2.67 (q, 4H, J=7.0), 3.14 (t, 2H, J=7.1), 4.08 (s, 3H), 4.17 (s, 3H), 4.64 (t, 2H, J=7.1), 6.25 (s, 2H), 7.80 (s, 1H), 7.84 (s, 1H), 8.18 (s, 1H), 8.63 (s, 1H); $^{13}$C NMR (CDCl$_3$) δ 11.8, 47.7, 48.0, 51.5, 56.4, 56.6, 99.7, 102.7, 104.3, 106.4, 108.0, 113.7, 119.7, 129.1, 131.1, 134.4, 149.4, 150.3, 151.2, 151.5, 154.4, 163.2; HRMS calcd for C$_{24}$H$_{26}$O$_5$N$_4$H: 451.1952; found: 451.1960.

EXAMPLE 3

2,3-Dimethoxy-8,9-methylenedioxy-11-[(2-dimethylamino)-1-methylethyl]-11H-5,6,11-triaza-chrysen-12-one: Prepared from N-(6,7-Methylenedioxycinnolin-4-yl)-N-[2-(N,N-dimethylamino)-1-methylethyl]-2-iodo-4,5-dimethoxybenzamide (100 mg, 0.18 mmol); (28% yield); reaction time 2 h; mp 235-36° C.; IR(KBr) 1659: $^1$H NMR (CDCl$_3$) δ 1.93 (d, 3H, J=8.2), 1.97 (s, 3H), 2.74 (dd, 1H, J=5.8, 13.6), 3.27 (dd, 1H, J=7.4, 12.8), 4.07 (s, 3H), 4.15 (s, 3H), 4.80 (m, 1H), 6.24 (s, 2H), 7.74 (s, 1H), 7.81 (s, 1H), 8.57 (s,1H); $^{13}$C (CDCl$_3$) δ 19.4,45.6, 56.3, 58.6, 63.0, 99.0, 102.6, 104.1, 106.2, 107.9, 114.2, 120.8, 125.6, 128.6, 131.0, 132.5, 132.8, 135.1, 149.2, 150.3, 150.6, 151.3, 154.2, 164.0; HRMS calcd for C$_{23}$H$_{24}$N$_4$O$_5$H 436.1747; found 436.1832.

EXAMPLE 4

2,3-Dimethoxy-8,9-methylenedioxy-11-(2-tetrahydofuranyl)methyl-11H-5,6,11-triazachrysen-12-one: Prepared from N-(6,7-Methylenedioxycinnolin-4-yl)-N-[2-(tetrahydrofuran-2-yl)methyl]-2-iodo-4,5-dimethoxybenzamide (140 mg, 0.25 mmol); (22% yield); reaction time 45 min; mp 300-303° C. (dec.); IR (CHCl$_3$) 1653; $^1$H NMR (CDCl$_3$) δ 1.79 (m, 1H), 2.00 (m, 2H), 2.25 (m, 1H), 3.87 (m, 2H), 4.09 (s, 3H), 4.18 (s, 3H), 4.65 (m, 3H), 6.25 (s, 2H), 7.80 (s, 1H), 7.84 (s, 1H), 8.32 (s, 1H), 8.63 (s, 1H); $^{13}$C NMR (CDCl$_3$) δ 25.7, 30.8, 53.0, 56.4, 56.7, 68.4, 77.8, 100.0, 102.7, 104.3, 106.3, 108.0, 114.1, 119.7, 129.1, 131.4, 134.5, 149.5, 150.2, 150.8, 151.4, 154.4, 163.7; HRMS calcd for C$_{23}$H$_{21}$O$_6$N$_3$: 435.1430; found: 435.1427.

EXAMPLE 5

2,3-Dimethoxy-8,9-methylenedioxy-11-[2-(pyrrolidin-1-yl)ethyl]-11H-5,6,11-triaza-chrysen-12-one: Prepared from N-(6,7-Methylenedioxycinnolin-4-yl)-N-[(2-pyrrolidin-1-yl)ethyl]-2-iodo-4,5-dimethoxybenzamide (150 mg, 0.2 mmol) in 24% yield with a reaction time 30 min; mp 229° C.; IR (KBr) 1644; $^1$H NMR (CDCl$_3$) δ 1.83 (m, 4H), 2.71 (m, 4H), 3.23 (t, 2H, J=7), 4.06 (s, 3H), 4.63 (t, 2H, J=7), 6.23 (s, 2H), 7.74 (s, 1H), 7.80 (s, 1H); $^{13}$C NMR (CDCl$_3$) δ 23.7, 54.0, 54.2, 56.3, 56.6, 99.4, 102.7, 104.2, 106.3, 107.7, 113.5, 119.4, 129.0, 134.1, 140.2, 150.2, 151.4, 154.3, 154.3, 163.0; HRMS calcd for C$_{24}$H$_{24}$N$_4$O$_5$H: 449.1825; found 449.1822.

EXAMPLE 6

2,3-Dimethoxy-8,9-methylenedioxy-11-[2-(piperidin-1-yl)ethyl]-11H-5,6,11-triaza-chrysen-12-one: Prepared from N-(6,7-Methylenedioxy-4-cinnolin-4-yl)-N-[2-(piperidin-1-yl)ethyl]-2-iodo-4,5-dimethoxybenzamide (295 mg, 0.5 mmol); (32.4% yield); reaction time 30 min; mp 294-95° C.; IR (KBr) 1662;$^1$HNMR (CDCl$_3$) δ 1.59 (s, 6H), 2.51 (s, 4H), 3.02 (t, 2H, J=6.6), 4.08 (s, 3H), 4.17 (s, 3H), 4.64 (t, 2H, J=6.6), 6.26 (s, 2H), 7.81 (s,1H), 7.85 (s, 1H), 8.36 (s, 1H), 8.65 (s, 1H); $^{13}$C (CDCl$_3$) δ 24.3, 26.0, 47.5, 55.0, 56.3, 56.6, 57.4, 99.9, 102.7, 104.2, 106.3, 107.9, 113.7, 119.6, 129.0, 131.1, 134.3, 149.3, 150.2, 151.1, 151.4, 154.3, 163.1; HRMS calcd for C$_{25}$H$_{26}$N$_4$O$_5$H 463.1981; found 463.1986.

EXAMPLES 2.a-6.a

The intermediate 4-amino-6,7-methylenedioxycinnoline o-iodobenzamide derivatives used in Examples 2-6 were prepared using the following general procedure.

A 2.0M solution of oxalyl chloride in CH$_2$Cl$_2$ (1.3 equiv.) was added to a solution of 2-iodo-4,5-dimethoxybenzoic acid (1.0 equiv.) in anhydrous CH$_2$Cl$_2$ (≈60 mL per 10 mmol benzoic acid) and the solution stirred at reflux for 3 h. The mixture was allowed to cool and was then concentrated to dryness in vacuo. To the residues was added a solution of requsite 4-amino-6,7-dimethoxyquinoline (1.0 equiv), triethylamine (2 equiv.) in CH$_2$Cl$_2$ (≈60 mL per 4 mmol aminoquinoline). The reaction mixture was then stirred at reflux under N$_2$. The reaction mixture was cooled and washed with sat. NaHCO$_3$ and extracted with 3% HCl. The aqueous layer was neutralized with 20% NaOH and extracted with CHCl$_3$, dried (MgSO$_4$) and evaporated.

EXAMPLE 2.a.

N-(6,7-Methylenedioxycinnolin-4-yl)-N—(N,N-diethylaminoethyl)-2-iodo-4,5-dimethoxybenzamide: Prepared from N'-(6,7-Methylenedioxycinnolin-4-yl)-N,N-diethylethane-1,2-diamine (640 mg, 2.2 mmol); (87% yield); reaction time 16 h; IR (CHCl$_3$) 1656; $^1$H NMR (CDCl$_3$) δ 0.92 (t, 6H, J=7.0), 2.50 (q, 4H, J=7.0), 2.80 (t, 2H, J=6.8), 3.39 (s, 3H), 3.71 (s, 3H), 3.94 (m, 1H), 4.41 (m, 1H), 6.21 (d, 2H, J=1.4), 6.39 (s, 1H), 7.01 (s, 1H), 7.39 (s, 1H), 7.64 (s, 1H), 9.11 (s, 1H); $^{13}$C NMR (CDCl$_3$) δ 11.6, 46.9, 47.8, 51.1, 55.7, 56.1, 82.9, 96.9, 102.9, 105.5, 110.9, 122.1, 122.9, 133.0, 136.5, 144.9, 148.3, 150.1, 150.9, 151.7, 152.3, 169.8; HRMS calcd for C$_{24}$H$_{27}$O$_5$N$_4$IH: 579.1105; found: 579.1105.

EXAMPLE 3.a.

N-(6,7-Methylenedioxycinnolin-4-yl)-N-[2-(N,N-dimethylamino)-1-methylethyl]-2-iodo-4,5-dimethoxybenzamide: Prepared from N-(6,7-difluorocinnolin-4-yl)-N$^1$,N$^1$-dimethylpropane-1,2-diamine (240 mg, 0.87 mmol); (83% yield); reaction time 16 h, mp 110-111° C.; $^1$H NMR (CDCl$_3$) was a mixture of atropisomers δ isomer #1 1.03-1.36 (m, 3H), 2.21-2.37 (m, 6H), 2.74-3.07 (m, 1H), 3.43-3.65 (m, 6H), 3.84-3.91 (m, 1H), 5.15 (m, 1H), 6.18 (s, 2H), 6.59 (s, 1H), 6.91 (s, 1H), 7.56 (s, 1H), 8.04 (s, 1H), 9.34 (s, 1H) isomer #2 1.03-1.36 (m, 3H), 2.31-2.37 (m, 6H), 2.74-3.07 (m, 1H), 3.43-3.65 (m, 6H), 3.84-3.91 (m,1H), 5.15 (m, 1H), 6.18 (s, 2H), 6.59 (s, 1H), 6.91 (s, 1H), 7.56 (s, 1H), 8.04 (s, 1H), 9.34 (s, 1H); HRMS calcd for $C_{23}H_{25}O_5N_4IH$: 565.0870; found: 565.0926.

EXAMPLE 4.a.

N-(6,7-Methylenedioxycinnolin-4-yl)-N-[2-(tetrahydrofuran-2-yl)methyl]-2-iodo-4,5-dimethoxybenzamide: Prepared from 2-[[[N-(6,7-Methylenedioxycinnolin-4-yl)] amino]methyl]tetrahydrofuran (400 mg, 1.5 mmol); (34% yield); reaction time 16 h;; IR ($CHCl_3$) 1654; $^1$H NMR, a mixture of atropisomers, ($CDCl_3$) δ isomer #1 1.94 (m, 4H), 3.70 (m, 4H), 3.73 (s, 3H), 3.94 (s, 3H), 4.34 (m, 1H) 6.23 (s, 2H), 7.00 (s, 1H), 7.40 (s, 1H), 7.70 (s, 1H), 9.31 (s, 1H), isomer #2 1.94 (m, 4H), 3.70 (m, 4H), 3.73 (s, 3H), 3.94 (s, 3H), 4.34 (m, 1H) 6.46 (s, 2H), 7.36 (s, H), 7.49 (s, 1H), 7.65 (s, 1H), 9.17 (s, 1H); HRMS calcd for $C_{23}H_{22}O_6N_3IH$: 564.0632; found: 564.0650.

EXAMPLE 5.a.

N-(6,7-Methylenedioxycinnolin-4-yl)-N-[(2-pyrrolidin-1-yl)ethyl]-2-iodo-4,5-dimethoxybenzamide: Prepared from 1-[2-[N-(6,7-Methylenedioxycinnolin-4-yl)]amino]ethylpyrrolidine (400 mg, 0.4 mmol) in 42% yield with a reaction time 4 h at 50° C. from the acid chloride prepared using 4.1 mmol of oxalyl chloride and 1.6 mmol of 2-iodo-4,5-dimethoxybenzoic acid. Compound 8f had: IR (KBr) 1655; $^1$H NMR ($CDCl_3$) δ 1.60 (m, 4H), 2.40 (m, 4H), 2.67 (m, 2H), 3.28 (s, 3H), 3.60 (s, 3H), 4.32 (m, 1H), 6.11 (d, 2H, J=2.2), 6.32 (s, 1H), 6.91 (s, 1H), 7.37 (s, 1H), 7.50 (s, 1H), 9.04 (s, 1H); $^{13}$C NMR ($CDCl_3$) δ 23.6, 29.7, 47.6, 52.9, 53.9, 55.7, 56.0, 56.4, 82.8, 96.7, 102.9, 105.4, 110.6, 121.9, 123.1, 132.8, 135.9, 144.7, 148.2, 149.9, 150.9, 151.7, 152.4, 169.9.

EXAMPLE 6.a.

N-(6,7-Methylenedioxy-4-cinnolin-4-yl)-N-[2-(piperidin-2-yl)ethyl]-2-iodo-4,5-dimethoxybenzamide: Prepared from 1-[2-[N-(6,7-Methylenedioxycinnolin-4-yl)]amino] ethylpiperidine (500 mg, 1.66 mmol); (85.4% yield); reaction time overnight at 50° C. mp 93-94° C.; IR (KBr) 1655; $^1$HNMR ($CDCl_3$) δ 1.43 (m, 6H), 2.35 (m, 4H), 2.50-2.71 (m, 2H), 3.43 (s, 3H), 3.73 (s, 3H), 3.78-3.93 (m, 1H), 4.32.4.42 (m, 1H), 6.22 (d, 2H, J=1.6), 6.42 (s, 1H), 7.02 (s, 1H), 7.47 (s, 1H), 7.66 (s, 1H), 9.19 (s, 1H); $^{13}$C ($CDCl_3$) δ 24.3, 25.9, 46.0, 46.4, 54.5, 55.6, 56.0, 56.4, 82.9, 97.0, 102.8, 105.3, 110.8, 122.0, 113.7, 123.2, 133.1, 136.3, 145.0, 148.2, 149.9, 150.8, 151.6, 152.1, 169.8 HRMS calcd for $C_{23}H_{25}IN_4O_5H$: 591.1105; found 591.1108.

EXAMPLES 2.b-6.b

The intermediate 4-amino-6,7-dimethoxyquinoline derivatives used in Examples 2.a-6.a. were prepared using the following general procedure.

The appropriate primary amine (1.0 mol equiv.) added with stirring to 4-Chloro-6,7-methylenedioxycinnoline (see Example 1 above). The reaction was then allowed to stir at 100° C. for several hours, and the phenol removed by Kugelrohr distillation under reduced pressure. The residue was partitioned between $CHCl_3$ and 10% NaOH. The aqueous layer was repeatedly separated with $CHCl_3$. All of the $CHCl_3$ solutions (initial partition and extracts) were combined and dried ($MgSO_4$).

EXAMPLE 2.b.

N'-(6,7-Methylenedioxycinnolin-4-yl)-N,N-diethylethane-1,2-diamine: Prepared from 4-Chloro-6,7-methylenedioxycinnoline (1.0 g, 4.8 mmol); (70% yield); reaction time 3 h; mp 230-232° C.; $^1$H NMR ($CDCl_3$) δ 1.10 (t, 6H, J=7.2), 2.63 (q, 4H, J=7.2), 2.84 (t, 2H, J=5.7), 3.35 (q, 2H, J=5.7), 5.78 (br, 1H), 6.15 (s, 2H), 6.96 (s, 1H), 7.57 (s, 1H), 8.52 (s, 1H); $^{13}$C NMR ($CDCl_3$) δ 12.2, 39.5, 46.6, 50.8, 94.4, 102.0, 105.4, 112.8, 129.0, 139.8, 147.8, 149.5, 150.7; HRMS calcd for $C_{15}H_{20}O_2N_4$: 288.1586; found: 288.1575.

EXAMPLE 3.b.

N-(6,7-difluorocinnolin-4-yl)-$N^1$,$N^1$-dimethylpropane-1, 2-diamine: Prepared from 4-Chloro-6,7-methylenedioxycinnoline (0.52 g, 2.5 mmol); (42% yield), reaction time 4 h, mp 196-197° C.;; $^1$H NMR ($CD_3OD$) δ 1.31 (d, 3H, J=6.6), 2.33 (s, 6H), 2.45 (dd, 1H, J=5.4, 12.8), 2.74 (dd, 1H, J=8.2, 12.6), 4.12 (dd, 1H, J=5.8, 13.8), 6.19 (s, 2H), 7.32 (s, 1H), 7.56 (s, 1H), 8.51 (s, 1H); $^{13}$C NMR ($CD_3OD$) δ 17.1, 44.0, 45.3, 63.5, 95.1, 101.6, 102.0, 112.6, 126.7, 140.8, 149.3, 151.2; HRMS calcd for $C_{14}H_{18}O_2N_4$: 274.1430; found: 274.1429.

EXAMPLE 4.b.

2-[[[N-(6,7-Methylenedioxycinnolin-4-yl)]amino]methyl]tetrahydrofuran: prepared from 4-Chloro-6,7-methylenedioxycinnoline (500 mg, 2.4 mmol); (78% yield); reaction time 2 h; mp 196-198° C.; $^1$H NMR ($CDCl_3$) δ 1.74 (m, 1H), 2.11 (m, 3H), 3.30 (m, 1H), 3.58 (m, 1H), 3.92 (m, 2H), 4.29 (m, 1H), 5.22 (br, 1H), 6.12 (s, 2H), 6.98 (s, 1H), 7.52 (s, 1H), 8.54 (s, 1H); $^{13}$C NMR ($CDCl_3$) δ 25.9, 29.2, 46.9, 68.4, 76.9, 94.4, 102.2, 105.2, 112.8, 128.7, 139.8, 147.9, 149.6, 150.8; HRMS calcd for $C_{14}H_{15}O_3N_3$: 273.1130; found: 273.1130.

EXAMPLE 5.b.

1-[2-[N-(6,7-Methylenedioxycinnolin-4-yl)]amino]ethylpyrrolidine: Prepared from 4-Chloro-6,7-methylenedioxycinnoline (750 mg, 3.5 mmol), 1-(2-aminoethyl)pyrrolidine (3 ml) and copper powder (300 mg) in 75% yield; reaction time 18 h at 90° C.; mp 215° C. (dec); $^1$H NMR ($CDCl_3$) δ 1.85 (m, 4H), 2.63 (m, 4H), 2.90 (t, 2H, J=6), 3.42 (t, 2H, J=6), 5.63 (s, 1H), 6.14 (s, 2H), 7.04 (s, 1H), 7.57 (s, 1H), 8.53 (s, 1H); $^{13}$C NMR (DMSO-$d_6$) δ 23.9, 42.0, 54.5, 54.7, 97.0, 102.9, 104.4, 112.7, 126.8, 140.8, 149.3, 151.0; HRMS calcd for $C_{15}H_{18}N_4O_2$: 293.1590; found 293.1579.

EXAMPLE 6.b.

1-[2-[N-(6,7-Methylenedioxycinnolin-4-yl)]amino]ethylpiperidine: Prepared from 4-Chloro-6,7-methylenedioxycinnoline (1.04 g, 5.0 mmol); (37% yield); reaction time 2 h; mp 238-239° C.; $^1$H NMR ($CD_3OD$) δ 1.56 (d, 2H, J=5.2), 1.70 (d, 2H, J=4.6), 2.87 (t, 2H, J=7), 3.65 (t, 2H, J=6.6), 6.20 (s, 2H), 7.32 (s, 1H), 7.43 (s, 1H), 8.46 (s, 1H); $^{13}$C ($CD_3OD$) δ 23.1, 24.7, 38.5, 53.6, 56.1, 94.7, 101.7, 102.1, 112.4, 126.6, 141.1, 14.7, 149.4, 151.2 ($CDCl_3$);HRMS calcd for $C_{16}H_{20}N_4O_2H$: 300.1586; found 300.1586.

EXAMPLES 7-12

The representative compounds of the invention at Examples 7-12 were prepared using the following general procedure from the intermediates prepared in the correspondingly numbered sub-parts a below.

A mixture of the requsite 4-amino-6,7-methylenedioxyquinoline o-iodobenzamide derivative (1.0 mmol equiv.), Pd(OAc)$_2$ (0.2 mmol equiv.), P(o-tolyl)$_3$ (0.4 mmol equiv.), and Ag$_2$CO$_3$ (2.0 mmol equiv) was heated to reflux in DMF (30 mL per mmol equiv.) with stirring. The reaction mixture was allowed to cool to room temperature, diluted with CHCl$_3$, and filtered through Celite. The sicciate was extensively washed with 10% CH$_3$OH in CHCl$_3$. The filtrate was concentrated in vacuo and the residue chromatographed on silica gel using chloroform:methanol.

EXAMPLE 7

8,9-Dimethoxy-2,3-methylenedioxy-5-[2-(N,N-dimethylamino)ethyl]-5H-dibenzo[c,h]1,6-naphthyridin-6-one. Prepared from N-(6,7-Methylenedioxyquinolin-4-yl)-N—(N,N-dimethylaminoethyl)-2-iodo-4,5-dimethoxybenzamide; (41% yield); reaction time 25 min; mp 283-285° C. (dec.); IR (CHCl$_3$) 1653; $^1$H NMR (CDCl$_3$) δ 2.33 (s, 6H), 3.04 (t, 2H, J=7.2), 4.07 (s, 3H), 4.14 (s, 3H), 4.64 (t, 2H, J=7.2), 6.18 (s, 2H), 7.47 (s, 1H), 7.68 (s, 1H), 7.89 (s, 2H), 9.37 (s, 1H); $^{13}$C NMR (CDCl$_3$) δ 45.9, 49.2, 56.3, 56.3, 57.9, 101.2, 102.0, 102.3, 107.1, 108.8, 111.7, 114.8, 119.3, 127.6, 140.9, 143.5, 147.3, 147.7, 149.9, 150.3, 154.2, 164.1; HRMS calcd for C$_{23}$H$_{23}$N$_3$O$_5$H: 422.1716; found 422.1710.

EXAMPLE 8

8,9-Dimethoxy-2,3-methylenedioxy-5-[2-(N,N-dimethylamino)-1-methylethyl]-5H-dibenzo[c,h]1,6-naphthyridin-6-one: Prepared from N-(6,7-Methylenedioxyquinolin-4-yl)-N-[2-(N,N-dimethylamino)-1-methylethyl]-2-iodo-4,5-dimethoxybenzamide; (30.4% yield); reaction time 30 min; mp 186-187° C.; IR (KBr) 1649; $^1$H NMR (CDCl$_3$); δ 1.95-1.98 (m, 9H), 2.77 (dd, 1H, J=12.0, 8.0), 3.21 (dd, 1H, J=12.0, 8.0), 4.06 (s, 3H), 4.13 (s, 3H), 4.84-4.92 (m, 1H), 6.17 (s, 2H), 7.46 (s, 1H), 7.66 (s, 1H), 7.77 (s, 1H), 7.87 (s, 1H), 9.35 (s, 1H); $^{13}$C NMR (CDCl$_3$) δ 19.7, 45.5, 56.2, 56.3, 59.5, 63.1, 100.9, 101.9, 102.1, 107.0, 108.7, 112.4, 115.2, 120.5, 127.3, 142.6, 143.3, 147.0, 147.3, 149.9, 150.1, 154.0, 164.9; HRMS calcd for C$_{24}$H$_{25}$N$_3$O$_5$H: 436.1794; found 436.1863.

EXAMPLE 9

8,9-Dimethoxy-2,3-methylenedioxy-5-[2-(pyrrolidin-1-yl)ethyl]-5H-dibenzo[c,h]1,6-naphthyridin-6-one: Prepared from N-(6,7-Methylenedioxyquinolin-4-yl)-N-[(2-pyrrolidin-1-yl)ethyl]-2-iodo-4,5-dimethoxybenzamide; (36% yield); reaction time 30 min; mp 255-257° C. (dec.); IR (CHCl$_3$) 1653; $^1$H NMR (CDCl$_3$) δ 1.79 (m, 4H), 2.64 (m, 4H), 3.20 (t, 2H, J=7.1), 4.07 (s, 3H), 4.14 (s, 3H), 4.69 (t, 2H, J=7.1), 6.18 (s, 2H), 7.46 (s, 1H), 7.68 (s, 1H), 7.89 (s, 1H), 7.95 (s, 1H), 9.37 (s, 1H); $^{13}$C NMR (CDCl$_3$) δ 23.7, 49.6, 54.3, 56.3, 56.4, 56.4, 101.3, 102.0, 102.3, 107.0, 108.7, 111.7, 114.8, 119.3, 127.7, 140.9, 143.4, 147.3, 147.8, 150.0, 150.3, 154.2, 164.2; HRMS calcd for C$_{25}$H$_{25}$N$_3$O$_5$H: 448.1872; found 448.1872.

EXAMPLE 10

8,9-Dimethoxy-2,3-methylenedioxy-5-[2-(4-methylpiperazin-1-yl)ethyl]-5H-dibenzo[c,h]1,6-naphthyridin-6-one: Prepared from N-(6,7-Methylenedioxyquinolin-4-yl)-N-[2-(4-methyl-1-piperazinyl)ethyl]-2-iodo-4,5-dimethoxybenzamide; (18% yield); reaction time 25 min; mp 244-246° C.; IR (CHCl$_3$) 1651; $^1$H NMR (CDCl$_3$) δ 2.27 (s, 3H), 2.51 (m, 8H), 2.95 (t, 2H, J=6.2), 4.07 (s, 3H), 4.15 (s, 3H), 4.69 (t, 2H, J=6.2), 6.19 (s, 2H), 7.48 (s, 1H), 7.70 (s, 1H), 7.91 (s, 2H), 7.92 (s, 1H), 9.39 (s, 1H); $^{13}$C NMR (CDCl$_3$) δ 29.8, 45.9, 48.6, 53.0, 55.0, 56.4, 56.4, 101.2, 102.0, 102.2, 107.1, 108.9, 112.0, 115.0, 119.5, 127.6, 141.2, 143.4, 147.4, 147.2, 150.0, 150.3, 154.1, 164.4; HRMS calcd for C$_{26}$H$_{28}$N$_4$O$_5$H: 477.2138; found 477.2139.

EXAMPLE 11

8,9-Dimethoxy-2,3-methylenedioxy-5-[3-(N,N-dimethylamino)propyl]-5H-dibenzo[c,h]1,6-naphthyridin-6-one): Prepared from N-(6,7-Methylenedioxyquinolin-4-yl)-N-[3-(N,N-dimethylamino)propyl]-2-iodo-4,5-dimethoxybenzamide; (45% yield); reaction time 30 min; mp 262-264° C. (dec.); IR (CHCl$_3$) 1648; $^1$H NMR (CDCl$_3$) δ 2.29 (m, 8H), 2.45 (m, 2H), 4.07 (s, 3H), 4.14 (s, 3H), 4.53 (t, 2H, J=7.4), 6.19 (s, 2H), 7.48 (s, 1H), 7.65 (s, 1H), 7.69 (s, 1H), 7.90 (s, 1H), 9.40 (s, 1H); $^{13}$C NMR (CDCl$_3$) δ 26.9, 45.3, 49.2, 56.3, 56.4, 56.9, 100.8, 101.9, 102.3, 107.1, 108.7, 111.6, 114.9, 119.4, 127.5, 141.0, 143.6, 147.2, 147.7, 149.9, 150.3, 154.1, 164.1; HRMS calcd for C$_{24}$H$_{25}$N$_3$O$_5$H: 436.1872; found 436.1878.

EXAMPLE 12

8,9-Dimethoxy-2,3-methylenedioxy-5-(2-tetrahydofuranyl)methyl-5H-dibenzo[c,h]1,6-naphthyridin-6-one: Prepared from N-(6,7-Methylenedioxyquinolin-4-yl)-N-[2-(tetrahydrofuran-2-yl)methyl]-2-iodo-4,5-dimethoxybenzamide; (22% yield); reaction time 30 min; mp 270-273° C.; IR (CHCl$_3$) 1648; $^1$H NMR (CDCl$_3$) δ 1.87 (m, 4H), 3.72 (m, 2H), 4.07 (s, 3H), 4.14 (s, 3H), 4.68 (m, 3H), 6.18 (s, 2H), 7.48 (s, 1H), 7.69 (s, 1H), 7.90 (s, 1H), 8.04 (s, 1H), 9.39 (s, 1H); $^{13}$C NMR (CDCl$_3$) δ 25.6, 30.3, 54.7, 56.3, 56.4, 68.1, 77.3, 101.7, 102.2, 102.3, 107.0, 109.0, 112.1, 115.2, 119.5, 127.7, 141.2, 143.5, 147.2, 147.4, 149.9, 150.3, 154.2, 164.6; HRMS calcd for C$_{24}$H$_{22}$N$_2$O$_6$H 435.1556; found 435.1566.

EXAMPLES 7.a-12.a

The intermediate 4-amino-6,7-methylenedioxyquinoline o-iodobenzamide derivatives used in Examples 7-12 were prepared using the following general procedure.

A 2.0M solution of oxalyl chloride in CH$_2$Cl$_2$ (1.3 equiv.) was added to a solution of 2-iodo-5,6-dimethoxybenzoic acid (1.0 equiv.) in anhydrous CH$_2$Cl$_2$ (≈60 mL per 10 mmol benzoic acid) and the solution stirred at reflux for 3 h. The mixture was allowed to cool and was then concentrated to dryness in vacuo. To the residue was added a solution of appropriate 4-amino-6,7-dimethoxyquinoline (1.0 equiv), triethylamine (2 equiv.) in CH$_2$Cl$_2$ (≈60 mL per 4 mmol aminoquinoline). The reaction mixture was then stirred at reflux under N$_2$. In the case of those derivatives that have an alkylamine incorporated in their structure, the residue was partitioned between CHCl$_3$ and 10% NaOH. The aqueous layer was repeatedly separated with CHCl$_3$. All of the CHCl$_3$ solutions (initial partition and extracts) were combined and dried (MgSO$_4$). The aqueous layer was neutralized with 20% NaOH and extracted with CHCl$_3$, dried (MgSO$_4$) and evaporated.

EXAMPLE 7.a.

N-(6,7-Methylenedioxyquinolin-4-yl)-N—(N,N-dimethylaminoethyl)-2-iodo-4,5-dimethoxybenzamide. Prepared from N'-(6,7-Methylenedioxyquinolin-4-yl)-N,N- dimethylethane-1,2-diamine (1.0 g, 3.84 mmol) in 71% yield with a reaction time of 3 h, from the acid chloride prepared using 10 mmol of oxalyl chloride and 4.8 mmol of 2-iodo-5,6-dimethoxybenzoic acid. Compound 7a had: IR (CHCl$_3$) 1652; $^1$H NMR (CDCl$_3$) δ 2.74 (s, 6H), 2.66 (t, 2.H, J=7.0), 3.33 (s, 3H), 3.74 (s, 3H), 3.96 (m, 1H) 4.49, (m, 1H), 6.15 (s, 2H), 6.41 (s, 1H), 7.03 (s, 1H), 7.34 (d, 1H, J=4.8), 7.37 (s, 1H), 7.44 (s, 1H), 8.56 (d, 1H, J=4.8); $^{13}$C NMR (CDCl$_3$) δ 45.7, 46.9, 55.5, 56.1, 56.6, 82.7, 98.5, 102.2, 106.7, 110.2, 120.2, 121.5, 122.9, 121.5, 122.9, 133.8, 145.9, 148.0, 148.3, 148.5, 149.0, 149.6, 151.0, 170.0; HRMS calcd for C$_{23}$H$_{24}$IN$_3$O$_5$H: 550.0839; found 550.0823.

EXAMPLE 8.a.

N-(6,7-Methylenedioxyquinolin-4-yl)-N-[2-(N,N-dimethylamino)-1-methylethyl]-2-iodo-4,5-dimethoxybenzamide. Prepared from N'-(6,7-Methylenedioxyquinolin-4-yl)-N,N-dimethylpropane-1,2-diamine (273 mg, 1.0 mol) in 60.4% yield with a reaction time of 12 h, from the acid chloride prepared using 4.8 mmol of oxalyl chloride and 1.2 mmol of 2-iodo-5,6-dimethoxybenzoic acid. Compound 7b had: mp 82-84° C.; IR (KBr) 1648, 3415; HRMS calcd for C$_{24}$H$_{26}$IN$_3$O$_5$H 564.0917; found 564.0997

EXAMPLE 9.a.

N-(6,7-Methylenedioxyquinolin-4-yl)-N-[(2-pyrrolidin-1-yl)ethyl]-2-iodo-4,5-dimethoxybenzamide. Prepared from 1-[2-[N-(6,7-Methylenedioxyquinolin-4-yl)]amino]ethylpyrrolidine (285 mg, 1.0 mmol), in 87% yield with a reaction time of 12 h, from the acid chloride prepared using 4 mmol of oxalyl chloride and 1.36 mmol of 2-iodo-5,6-dimethoxybenzoic acid. Compound 7c had: IR (CHCl$_3$) 1650; $^1$H NMR (CDCl$_3$) δ 1.78 (m, 4H), 2.22 (m, 1H), 2.59 (m, 3H), 2.83 (t, 2H, J=6.6), 3.33 (s, 3H), 3.74 (s, 3H), 3.96 (d,1H, J=4), 4.54 (m, 1H), 6.15 (s, 1H), 6.42 (s, 1H), 7.03 (s, 1H), 7.34 (d, 1H, J=4.8), 7.36 (s, 1H), 7.44 (s, 1H), 8.55 (d, 1H, J=4.8); $^{13}$C NMR (CDCl$_3$) δ 23.7, 47.7 52.9, 54.1, 55.5, 56.1, 82.7, 98.4, 102.2, 106.7, 106.7, 120.1, 121.5, 122.9, 133.7, 145.9, 148.0, 148.3, 148.4, 149.0, 149.6, 151.0, 170.0; HRMS calcd for C$_{25}$H$_{26}$IN$_3$O$_5$H: 576.0995; found 576.1003.

EXAMPLE 10.a.

N-(6,7-Methylenedioxyquinolin-4-yl)-N-[2-(4-methyl-1-piperazinyl)ethyl]-2-iodo-4,5-dimethoxybenzamide. Prepared from 1-[2-[N-(6,7-Methylenedioxyquinolin-4-yl)]amino]ethyl-4-methylpiperazine (290 mg, 0.9 mmol) in 50% yield with a reaction time of 12 h, from the acid chloride prepared using 4.0 mmol of oxalyl chloride and 1.8 mmol of 2-iodo-5,6-dimethoxybenzoic acid. Compound 7d had: IR (CHCl$_3$) 1649; $^1$H NMR (CDCl$_3$) δ 2.29 (s, 3H), 2.51 (m, 10H), 3.35 (s, 3H), 3.75 (s, 3H), 3.95 (m, 1H), 4.46 (m, 1H), 6.15 (s, 1H), 6.42 (s, 1H), 7.03 (s, 1H), 7.35 (d, 1H, J=4.6), 7.36 (s, 1H), 7.48 (s, 1H), 8.57 (d, 1H, J=4.6); $^{13}$C NMR (CDCl$_3$) δ 46.0, 46.2, 53.1, 55.2, 55.5, 55.5, 56.0, 82.7, 98.7, 102.2, 106.7, 110.4, 120.3, 121.6, 123.0, 133.7, 146.0, 148.0, 148.4, 148.4, 148.9, 149.6, 151.0, 170.0; HRMS calcd for C$_{26}$H$_{29}$IN$_4$O$_5$H: 605.1261; found 605.1261.

EXAMPLE 11.a.

N-(6,7-Methylenedioxyquinolin-4-yl)-N-[3-(N,N-dimethylamino)propyl]-2-iodo-4,5-dimethoxybenzamide. Prepared from N'-(6,7-Methylenedioxyquinolin-4-yl)-N,N-dimethylpropane-1,3-diamine (273 mg, 1.0 mmol), in 79% yield with a reaction time of 12 h, from the acid chloride prepared using 4.0 mmol of oxalyl chloride and 1.36 mmol of 2-iodo-5,6-dimethoxybenzoic acid. Compound 7e had: IR (CHCl$_3$) 1650; $^1$H NMR (CDCl$_3$) δ 1.93 (m, 1H), 2.16 (m, 1H), 2.34 (s, 6H), 2.58 (m, 1H), 3.31 (s, 3H), 3.47 (m, 1H), 3.75 (s, 3H), 3.95 (m, 1H,), 4.55, (m, 1H), 6.16 (s, 1H), 6.39 (s, 1H), 7.04 (s, 1H), 7.28 (d, 1H, J=5.0), 7.31 (s, 1H), 7.38 (s, 1H), 8.56 (d, 1h, J=5.0); $^{13}$C NMR (CDCl$_3$) δ 25.8, 45.1, 47.2, 55.5, 56.1, 26.9, 82.7, 98.1, 102.3, 107.0, 110.1, 120.1, 121.5, 122.5, 133.5, 145.5, 148.1, 148.4, 148.6, 149.2, 149.7, 151.1, 170. 1; HRMS calcd for C$_{24}$H$_{26}$IN$_3$O$_5$H: 564.0995; found 564.0990.

EXAMPLE 12.a.

N-(6,7-Methylenedioxyquinolin-4-yl)-N-[2-(tetrahydrofuran-2-yl)methyl]-2-iodo-4,5-dimethoxybenzamide. Prepared from 2-[[[N-(6,7-Methylenedioxyquinolin-4-yl)]amino]methyl]tetrahydrofuran (272 mg, 1.0 mol) in 36% yield with a reaction time of 16 h, from the acid chloride prepared using 4.0 mmol of oxalyl chloride and 1.36 mmol of 2-iodo-5,6-dimethoxybenzoic acid. Compound 7g had: IR (CHCl$_3$) 1652; HRMS calcd for C$_{24}$H$_{23}$N$_2$O$_6$IH: 563.0679; found 563.0703.

EXAMPLES 7.b-12.b

The intermediate 4-amino-6,7-dimethoxyquinoline derivatives used in Examples 7.a-12.a. were prepared using the following general procedure.

4-Chloro-6,7-methylenedioxyquinoline was stirred in refluxing phenol (5.5 mol equiv.) for 2.5 h. The temperature was lowered to 100° C. and the primary amine (1.0 mol equiv.) added with stirring. The reaction was then allowed to stir at 100° C. for several hours, and the phenol removed by Kugelrohr distillation under reduced pressure. In the case of those derivatives that have an alkylamine incorporated in their structure, the residue was partitioned between CHCl$_3$ and 10% NaOH. The aqueous layer was repeatedly separated with CHCl$_3$. All of the CHCl$_3$ solutions (initial partition and extracts) were combined and dried (MgSO$_4$). Other 4-amino-6,7-methylenedioxyquinoline derivatives were purified by column chromatography.

EXAMPLE 7.b.

N'-(6,7-Methylenedioxyquinolin-4-yl)-N,N-dimethylethane-1,2-diamine was prepared from N,N-dimethylethylenediamine (2.55 g, 29 mmol) in 54% yield with a reaction time of 24 h. Compound 6a had: mp 193-194° C.; $^1$H NMR (CDCl$_3$) δ 2.32 (s, 6H), 2.70 (t, 2H, J=6.6), 3.29 (m, 2H), 5.62 (br, 1H), 6.10 (s, 2H), 6.36 (d, 1H, J=5.3), 7.10 (s, 1H), 7.34 (s, 1H), 8.40 (d, 1H, J=5.3); $^{13}$C NMR (CDCl$_3$) δ 40.1, 45.2, 57.2, 96.3, 98.9, 101.6, 106.5, 114.4, 145.2, 146.8, 148.9, 149.7, 150.1; HRMS calcd for C$_{14}$H$_{17}$N$_3$O$_2$: 260.1399; found 260.1377.

EXAMPLE 8.b.

N'-(6,7-Methylenedioxyquinolin-4-yl)-N,N-dimethylpropane-1,2-diamine was prepared from 2-methyl-2-(N,N-dimethylamino)ethylamine (2.55 g, 29 mmol) from in 30.7% yield with a reaction time of 24 h. Compound 6b had: mp 71-72° C.; $^1$H NMR (CD$_3$OD); δ 1.26 (d, 3H, J=5.6), 3.22 (s, 6H), 2.41 (dd, 1H, J=6.2, 12), 2.65 (dd, 1H, J=5.8, 12.2), 3.82-3.86 (m, 1H), 6.16 (s, 2H), 6.46 (d, 1H, J=5.8), 7.16 (s, 1H), 7.45 s,1H), 8.20 (d, 1H, J=6.0); $^{13}$C NMR δ 17.1, 44.0, 45.4, 63.6, 96.6, 97.3, 101.3, 101.8, 113.9, 144.8, 146.3, 146.8, 149.7, 150.0; HRMS calcd for $C_{15}H_{19}N_3O_2H$: 273.1484; found 273.1477.

EXAMPLE 9.b.

1-[2-[N-(6,7-Methylenedioxyquinolin-4-yl)]amino]ethylpyrrolidine was prepared from 1-(2-aminoethyl)pyrrolidine (1.14 g, 10.0 mmol) in 31% yield with a reaction time of 20 h. Compound 6c had: mp 179-182° C.; $^1$H NMR (CDCl$_3$) δ 1.83 (m, 4H), 2.60 (m, 4H), 2.87 (t, 2H, J=5.9), 3.33 (m, 2H), 5.58 (br, 1H), 6.08 (s, 2H), 6.34 (d, 1H, J=5.1), 7.08 (s, 1H), 7.31 (s, 1H), 8.40 (d, 1H, J=5.1); $^{13}$C NMR (CDCl$_3$) δ 23.7, 41.4, 53.9, 54.0, 96.3, 98.9, 101.6, 106.6, 114.4, 146.4, 146.7, 149.1, 149.6, 150.0; HRMS calcd for $C_{16}H_{19}N_3O_2$: 285.1477; found 285.1468.

EXAMPLE 10.b.

1-[2-[N-(6,7-Methylenedioxyquinolin-4-yl)]amino]ethyl-4-methylpiperazine was prepared from 2-(4-methylpiperidin-1-yl)ethylamine (1.43 g, 10.0 mmol) in 20% yield with a reaction time of 24 h. Compound 6d had: mp 159-161° C.; $^1$H NMR (CDCl$_3$) δ 2.34 (s, 3H), 2.54 (m, 10H), 2.80 (t, 2H, J=5.9), 5.62 (br, 1H), 6.11 (s, 2H), 6.38 (d, 1H, J=5.2), 7.05 (s, 1H), 7.33 (s, 1H), 8.41 (d, 1H, J=5.2); $^{13}$C NMR (CDCl$_3$) δ 39.1, 46.2, 52.7, 55.4, 55.7, 96.0, 99.0, 101.6, 106.6, 114.3, 146.8, 146.8, 149.0, 149.5, 150.0; HRMS calcd for $C_{17}H_{22}N_4O_2$: 314.1743; found 314.1738.

EXAMPLE 11.b.

N'-(6,7-Methylenedioxyquinolin-4-yl)-N,N-dimethylpropane-1,3-diamine was prepared from N,N-dimethyl-1,3-diaminopropane (1.0 g, 10.0 mmol) in 25% yield with a reaction time of 20 h. Compound 6e had: mp 178-181° C.; $^1$H NMR (CDCl$_3$) δ 1.92 (m, 2H), 2.39 (s, 6H), 2.58 (t, 2H, J=5.5), 3.39 (m, 2H), 6.08 (s, 2H), 6.29 (d, 1H, J=5.6), 6.95 (s, 1H), 7.31 (s, 1H), 7.52 (br s, 1H), 8.37 (d, 1H, J=5.6); $^{13}$C NMR (CDCl$_3$) δ 24.6, 44.4, 45.7, 59.7, 96.6, 98.0, 101.5, 106.4, 114.5, 146.2, 146.6, 148.9, 149.9, 150.5.; HRMS calcd for $C_{15}H_{19}N_3O_2$: 273.1477; found 273.1473.

EXAMPLE 12.b.

2-[[[N-(6,7-Methylenedioxyquinolin-4-yl)]amino]methyl]tetrahydrofuran was prepared from tetrahydofurfurylamine (1.01 g, 10.0 mmol) in 84% yield with a reaction time of 20 h. Compound 6g had: mp 276-278° C.; $^1$H NMR (CD$_3$OD) δ 1.77 (m, 1H), 2.07 (m, 3H), 3.61 (m, 2H), 3.86 (m, 2H), 4.26 (m, 1H), 6.28 (s, 2H), 6.90 (d, 1H, J=7.1), 7.19 (s, 1H), 7.74 (s, 1H), 8.21 (d, 1H, J=7.1); $^{13}$C NMR (CDCl$_3$) δ 24.7, 28.1, 46.6, 67.3, 76.7, 96.5, 97.6, 97.8, 103.1, 112.2, 135.8, 138.6, 148.3, 153.2, 155.1; HRMS calcd for $C_{15}H_{16}N_2O_3$: 272.1161; found 272.1172.

The intermediate 4-Chloro-6,7-methylenedioxyquinoline was prepared as follows.

Diethyl 3,4-methylenedioxyanilinomethylene malonate. 3,4-Methylenedioxyaniline (41.0 g, 0.3 mmol) and diethyl ethoxymethylenemalonate (64.8g, 0.3 mmol) were refluxed in benzene for 3.5 hours. The solvent was evaporated in vacuo and the residue was washed with petroleum ether to give 88.3 g as a shiny grey-brown solid, in 96% yield; mp 99.5-101.0° C. (lit.[221] mp 102° C.); $^1$H NMR (CDCl$_3$) δ 1.34 (t, 3H, J=7.0), 1.40 (t, 3H, J=7.0) 4.25 (q, 2H, J=7.0), 4.31 (q, 2H, J=7.0), 6.01 (s, 2H), 6.60 (dd, 1H, J=8.5, J=2.2), 6.71 (d, 1H, J=2.2), 6.81 (d, 1H, J=8.5), 8.41 (d, 1H, J=14.0); $^{13}$C NMR (CDCl$_3$) δ 14.4, 14.6, 60.1, 60.4, 92.9, 99.4, 101.8, 108.9, 110.9, 134.3, 145.3, 148.9, 152.6, 165.8, 169.3.

4-Hydroxy-6,7-methylenedioxy-3-quinolinecarboxylic acid ethyl ester. Diethyl 3,4-methylenedioxyanilinomethylene malonate (80.0 g, 0.261 mol) was stirred in polyphosphate ester (PPE) (250 g, 0.528 mol) at 120° C. with a mechanical stirrer for 2 hours. The reaction mixture was poured into ice water (700 mL) and stirred until homogenous. The mixture was then neutralized (pH 8) with ammonium hydroxide, and the precipitate was filtered, washed well with water, and dried to give 54.7 g as a brown solid, in 80% yield; mp 277-278° C.; $^1$H NMR (DMSO-d$_6$) δ 1.26 (t, 3H, J=7.0), 4.16 (q, 2H, J=7.0), 6.09 (s, 2H), 7.02 (s, 1H), 7.38 (s, 1H), 8.48 (s, 1H).

4-Hydroxy-6,7-methylenedioxy-3-quinolinecarboxylic acid. 4-Hydroxy-6,7-methylenedioxy-3-quinolinecarboxylic acid ethyl ester (45.0 g, 0.172 mol) was added to a solution of KOH (16.8 g, 0.258 mol) in ethanol (500 mL) and the mixture was heated to reflux with stirring for 20 hours. The reaction flask was then cooled and ethanol was evaporated under reduced pressure. Then 800 mL of water were added with stirring to fully dissolve the potassium salt, and the solution was filtered to remove any impurities. Concentrated HCl was added to bring the mixture to pH 1, and the free acid was filtered off and dried under vacuum, to give 33.9 g as a beige solid, in 84%; mp >300° C. (lit.[221] mp>290° C.); $^1$H NMR (DMSO-d$_6$) δ 6.27 (s, 2H), 7.30 (s, 1H), 7.55 (s, 1H), 8.72 (s, 1H); $^{13}$C NMR (DMSO-d$_6$) δ 98.5, 101.8, 103.8, 107.9, 120.8, 137.9, 143.5, 148.1, 153.7, 167.4, 177.4.

6,7-Methylenedioxy-4-quinolone. A suspension of 4-hydroxy-6,7-methylenedioxy-3-quinolinecarboxylic acid (30 g, 0.129 mol) in diphenyl ether (320 mL) was heated to reflux with vigorous stirring. The reaction was carefully monitored until it became clear, about 1.5 h, and then immediately removed from heat. By this time all of the starting material had dissolved but a black tarry residue remained. The solution was decanted and cooled, allowing the product to precipitate. This material was filtered and washed with ethyl ether to remove all traces of phenyl ether. A second crop was obtained by vigorously washing the tarry residue with ethanol (16×250 mL), filtering and evaporating the ethanol, and rinsing the material with ethyl ether. The total yield was 14.9 g as a pale yellow solid, in 61%; mp 285-289° C. (lit.[221] mp 276° C.); $^1$H NMR (DMSO-d$_6$) δ 5.95 (d, 1H, J=7.3), 6.13 (s, 2H), 6.97 (s, 1H), 7.38 (s, 1H), 7.77 (d, 1H, J=7.3); $^{13}$C NMR (DMSO-d$_6$) δ 97.5, 102.1, 102.6, 108.7, 119.4, 122.0, 130.8, 138.7, 145.8, 151.7.

4-Chloro-6,7-methylenedioxyquinoline. 6,7-Methylenedioxy-4-quinolone (5.0 g, 26.5 mmol) was boiled in POCl$_3$ (75 mL) for 45 min and then cooled. Excess phosphoryl chloride was removed under reduced pressure and ice water (100 mL) was added to hydrolyze any residual phosphoryl chloride. The mixture was basified (pH 9) with ammonium hydroxide, and the solid precipitate was filtered. This material was extracted into ethyl ether (8×100 mL), and the ether solution was dried (MgSO$_4$) and evaporated to provide 4.55 g as a white solid, in 83%; mp 127.5-128° C. (lit. mp 129° C.); $^1$H NMR (CDCl$_3$) δ 6.15 (s, 2H), 7.35 (d, 1H, J=4.7), 7.39 (s, 1H), 7.49 (s, 1H), 8.56 (d, 1H, J=4.7); $^{13}$C NMR (CDCl$_3$) δ 99.8, 102.2, 106.1, 119.9, 123.7, 129.8, 141.2, 147.7, 149.1, 151.4.

EXAMPLES 13-16

The representative compounds of the invention at Examples 13-16 were prepared by deprotection of the corresponding tert-butyldimethylsilyl ethers (13-15) or the corresponding acetal as described below.

EXAMPLE 13

8,9-Dimethoxy-2,3-methylenedioxy-5-[2-(hydroxy)ethyl]-5H-dibenzo[c,h]1,6-naphthyridin-6-one: Prepared from the corresponding tert-butyldimethylsilyl ether (Example 13.a.) by treatment with AcOH, THF, $H_2O$ (3:1:1) at room temperature; (84% yield); reaction time 48 h; mp 285-286° C.; IR (KBr); 1653, 3448; $^1$H NMR (DMSO-$d_6$); δ 3.91 (s, 3H), 4.04 (s, 3H), 4.54 (t, 2H, J=4.4), 4.96 (t, 2H, J=4), 6.26 (s, 2H), 7.44 (s, 1H), 7.71 (s, 1H), 7.98 (s, 1H), 8.03 (s, 1H), 9.64 (s, 1H); $^{13}$C NMR (DMSO-$d_6$); δ 52.6, 56.4, 57.0, 59.5, 101.9, 103.0, 104.0, 106.8, 108.8, 111.9, 114.8, 119.1, 128.0, 141.2, 144.9, 147.4, 147.7, 150.2, 150.5, 154.6, 163.7; HRMS calcd ($M^+$-OH) for $C_{21}H_{17}O_5N_2$ 377.1137; Found 377.1121.

EXAMPLE 14

8,9-Dimethoxy-2,3-methylenedioxy-5-[2-(2-hydroxyethoxy)ethyl]-5H-dibenzo[c,h]1,6-naphthyridin-6-one: Prepared from the corresponding tert-butyldimethylsilyl ether (Example 14.a.) by treatment by treatment with AcOH, THF, $H_2O$ (3:1:1) at room temperature; (76% yield); reaction time 18 h; mp 235° C.; IR (KBr) 1654; $^1$H NMR (CDCl$_3$); δ 3.61 (t, 2H, J=5.2), 3.73 (t, 2H, J=5.2), 4.07 (s, 3H), 4.14 (s,3H), 4.22 (t, 2H, J=5.6), 4.71 (t, 2H, J=5.6), 6.2 (s, 2H), 7.53 (s, 1H), 7.69 (s, 1H), 7.88 (s, 1H), 8.05 (s, 1H), 9.39 (s, 1H). HRMS calcd for $C_{23}H_{22}N_2O_7H$: 439.1506; found 439.1499.

EXAMPLE 15

8,9-Dimethoxy-2,3-methylenedioxy-5-[2-N,N-dimethylamino-1-(hydroxymethyl)ethyl]-5H-dibenzo[c,h]1,6-naphthyridin-6-one: Prepared from the corresponding tert-butyldimethylsilyl ether (Example 15.a.) by treatment with 5N HCl in isopropanol at room temperature for 30 min; (57% yield); reaction time 30 min; mp 132° C.; IR (KBr) 1647; $^1$H NMR (CDCl$_3$); δ 2.00 (s, 6H), 2.72-2.81 (m, 1H), 3.16-3.26 (m, 1H), 4.05 (s, 3H), 4.12 (s, 3H), 4.20-4.28 (m, 1H), 4.65-4.73 (m, 1H), 4.98 (m, 1H), 6.17 (q, 2H, J=1.2), 7.44 (s, 1H), 7.51 (s, 1H), 7.64 (s, 1H), 7.82 (s, 1H), 7.82 (s, 1H); 9.33 (s, 1H); $^{13}$C NMR (CDCl$_3$) δ: 45.6, 56.2, 56.3, 60.0, 64.1, 65.2, 100.9, 101.8, 102.3, 106.6, 108.5, 112.5, 115.0, 119.6, 127.5, 141.1, 143.0, 147.1, 147.5, 149.9, 150.0, 154.1, 165.0.

EXAMPLE 16

8,9-Dimethoxy-2,3-methylenedioxy-5-[2,3-dihydroxy)propyl]-5H-dibenzo[c,h]1,6-naphthyridin-6-one: Prepared from the corresponding acetal (Example 16.a.) by treatment 80% AcOH at reflux for 2 h. The reaction mixture was allowed to cool, and then concentrated in vacuo. The crude residue was triturated with chloroform (1.5 mL), filtered, and washed with additional chloroform (10 mL), to provide 16.5 mg of pure material, in 60% yield; mp 272-274° C. (dec.); IR (KBr) 1631, 3407; $^1$H NMR (DMSO-$d_6$) δ 3.31 (d, 2H, J=8.0), 3.95 (s, 3H), 4.07 (s, 3H), 4.63 (m, 3H), 6.33 (s, 2H), 7.55 (s, 1H), 7.72 (s, 1H), 8.06 (s, 2H), 8.21 (s, 1H), 9.79 (s, 1H); $^{13}$C NMR (DMSO-$d_6$) δ 54.4, 56.5 57.3, 64.9, 68.8, 103.2, 103.8, 104.6, 108.9, 109.0, 112.6, 115.5, 119.3, 127.3, 138.5, 140.6, 148.2, 151.0, 151.3, 151.8, 154.8, 163.9; HRMS calcd for $C_{22}H_{20}N_2O_7H$: 425.1350; found 425.1359.

EXAMPLES 13.a-16.a

The intermediate iodo compounds of Examples 13.b.-16.b. were cyclized using the following general procedure.

A mixture of the requsite 4-amino-6,7-methylenedioxyquinoline o-iodobenzamide derivative (1.0 mmol equiv.), Pd(OAc)$_2$ (0.2 mmol equiv.), P(o-tolyl)$_3$ (0.4 mmol equiv.), and Ag$_2$CO$_3$ (2.0 mmol equiv) was heated to reflux in DMF (30 mL per mmol equiv.) with stirring. The reaction mixture was allowed to cool to room temperature, diluted with CHCl$_3$, and filtered through Celite. The sicciate was extensively washed with 10% CH$_3$OH in CHCl$_3$. The filtrate was concentrated in vacuo and the residue chromatographed on silica gel using chloroform:methanol.

EXAMPLE 13.a.

Prepared from N-(6,7-Methylenedioxyquinolin-4-yl)-N-[(2-(t-butyldimethylsilanyloxy)-ethyl]-2-iodo-4,5-dimethoxybenzamide (36.4% yield); reaction time 30 min; mp 271-273° C.; IR (KBr) 1658; $^1$H NMR (CDCl$_3$) δ 0.00 (s, 6H), 0.68 (s, 9H), 4.04 (s, 3H), 4.12 (s, 3H), 4.24 (t, 2H, J=8), 4.65 (t, 2H, J=8), 6.18 (s, 2H), 7.44 (s, 1H), 7.64 (s, 1H), 7.85 (s, 1H), 8.01 (s, 1H) 9.29 (s, 1H); HRMS calcd for $C_{27}H_{33}ISiN_2O_6H$: 637.1153; found 637.1212

EXAMPLE 14.a.

Prepared from N-(6,7-Methylenedioxyquinolin-4-yl)-N-[2-(2-(t-butyldimethylsilanyloxy)ethoxy)ethyl]-2-iodo-4,5-dimethoxybenzamide; (75% yield); reaction time 18 h; mp 238° C. (dec.); IR (KBr): 1639; $^1$H NMR (CDCl$_3$); δ 0.00 (s, 6H), 0.85 (s, 9H), 3.54 (t, 2H, J=5.2), 3.70 (t, 2H, J=5.2), 4.07 (s, 3H), 4.14 (s,3H), 4.16 (t, 2H, J=6.0), 4.71 (t, 2H, J=6.0), 6.17 (s, 2H), 7.48 (s, 1H) 7.70 (s, 1H), 7.94 (s, 1H), 9.39 (s, 1H); HRMS calcd for $C_{23}H_{23}N_2O_7H$: 439.1505; found 439.1506.

EXAMPLE 15.a.

Prepared from N-(6,7-Methylenedioxyquinolin-4-yl)-N-[1-[(t-butyldimethylsilanyloxy)-methyl]-N-2-dimethylaminoethyl]]-2-iodo-4,5-dimethoxybenzamide (95% yield); reaction time 45 min; $^1$H NMR (CDCl$_3$); δ 0.13 (6H), 069 (s, 9H), 1.97(s, 6H), 1.92 (s, 6H), 2.52 (m, 1H), 2.80 (m, 1H) 3.20 (m, 1H), 4.01 (s, 3H), 4.09(s, 3H), 4.50 (m, 1H), 4.90 (m, 1H), 6.11 (m,2H), 7.30 (s, 1H), 7.61 (s, 1H) , 7.79 (s, 1H), 8.19 (s, 1H), 9.32 (s, 1H).

EXAMPLE 16.a.

8,9-Dimethoxy-2,3-methylenedioxy-5-[2,2-dimethyl[1,3]dioxolan-4-yl]methyl]-5H-dibenzo[c,h]1,6-naphthyridin-6-one was prepared from N-(6,7-Methylenedioxyquinolin-4-yl)-N-[(2,3-dihydroxy)propyl]-2-iodo-5,6-dimethoxybenzamide (22% yield); reaction time 45 min); mp 241-244° C. (dec.); IR (CHCl$_3$) 1652; $^1$H NMR (CDCl$_3$) δ 1.34 (s, 3H), 1.36 (s, 3H), 3.95 (m, 2H), 4.08 (s, 3H), 4.14 (s, 3H), 4.35 (m, 1H), 4.55 (m, 1H), 4.77 (m, 1H), 6.19 (s, 2H), 7.48 (s, 1H), 7.70 (s, 1H), 7.87 (s, 2H), 8.05 (s, 1H), 9.40 (s, 1H); $^{13}$C NMR (CDCl$_3$) δ 25.5, 26.5, 54.0, 56.3, 56.4, 69.4, 75.5, 101.6, 102.1, 102.3, 107.0, 108.7, 109.7, 111.8, 114.9, 119.1, 127.8, 141.1, 143.5, 147.4, 147.7, 150.1, 150.4, 154.4, 164.6; HRMS calcd for $C_{25}H_{24}N_2O_7H$ 465.1662; found 435.1677.

The compound 8,9-Dimethoxy-2,3-methylenedioxy-5-[2,2-dimethyl[1,3]dioxolan-4-yl]methyl]-5H-dibenzo[c,h]1,6-naphthyridin-6-one is also a compound of the invention.

EXAMPLES 13.b.-16.b.

The intermediate 4-amino-6,7-methylenedioxyquinoline o-iodobenzamide derivatives used in Examples 13.a.-1 6.a. were prepared using the following general procedure.

A 2.0M solution of oxalyl chloride in $CH_2Cl_2$ (1.3 equiv.) was added to a solution of 2-iodo-5,6-dimethoxybenzoic acid (1.0 equiv.) in anhydrous $CH_2Cl_2$ (≈60 mL per 10 mmol benzoic acid) and the solution stirred at reflux for 3 h. The mixture was allowed to cool and was then concentrated to dryness in vacuo. To the residue was added a solution of appropriate 4-amino-6,7-dimethoxyquinoline (1.0 equiv), triethylamine (2 equiv.) in $CH_2Cl_2$ (≈60 mL per 4 mmol aminoquinoline). The reaction mixture was then stirred at reflux under $N_2$. In the case of those derivatives that have an alkylamine incorporated in their structure, the residue was partitioned between $CHCl_3$ and 10% NaOH. The aqueous layer was repeatedly separated with $CHCl_3$. All of the $CHCl_3$ solutions (initial partition and extracts) were combined and dried ($MgSO_4$). The aqueous layer was neutralized with 20% NaOH and extracted with $CHCl_3$, dried ($MgSO_4$) and evaporated.

EXAMPLE 13.b.

N-(6,7-Methylenedioxyquinolin-4-yl)-N-[(2-(t-butyldimethylsilanyloxy)-ethyl]-2-iodo-4,5-dimethoxybenzamide. Prepared from 4-[N-[2-(t-Butyldimethylsilanyloxy)]ethyl]amino-6,7-methylenedioxyquinoline (400 mg, 1.15 mmol) in 51.7% yield with a reaction time of 12 h, from the acid chloride prepared using 5.0 mmol of oxalyl chloride and 1.38 mmol of 2-iodo-5,6-dimethoxybenzoic acid. Compound 8h had: mp 79-80° C.; IR (KBr); 1653 $^1$H NMR (CDCl$_3$); δ 0.004 (d, 3H, J=4.2 Hz), 0.82 (s, 9H), 3.26 (s, 3H), 3.67 (s, 3H), 3.84-4.02 (m, 4H), 6.13 (d, 2H, J=4 Hz), 6.40 (s, 1H), 7.02 (s, 1H), 7.33 (d, 1H, J=4.2 Hz), 7.36 (s, 1H), 7.42 (s, 1H), 8.52 (d, 1H, J=4 Hz); HRMS calcd for $C_{27}H_{33}ISiN_2O_6H$ 637.1232; observed 637.1212

EXAMPLE 14.b.

N-(6,7-Methylenedioxyquinolin-4-yl)-N-[2-(2-(t-butyldimethylsilanyloxy)ethoxy)ethyl]-2-iodo-4,5-dimethoxybenzamide. Prepared from 4-[N-[2-[2-(t-Butyldimethylsilanyloxy)ethoxy]ethyl]ethyl]amino-6,7-methylenedioxyquinoline (354 mg, 9.0 mmol) in 60% yield with a reaction time of 24 h, from the acid chloride prepared using 4.5 mmol of oxalyl chloride and 1.8 mmol of 2-iodo-5,6-dimethoxybenzoic acid. Compound 8i had: $^1$H NMR (CDCl$_3$); δ 0.006 (s, 6H), 0.83 (s, 9H), 3.27 (s, 3H), 3.48 (t, 2H, J=4.6), 3.67 (t, 2H, J=5.6), 3.69 (s, 3H), 3.76-4.55 (m, 4H), 6.10 (s, 2H), 6.36 (s, 1H), 6.99 (s, 1H), 7.30-7.32 (three singlets, 3H), 8.52 (d, 1H, J=4.8).

EXAMPLE 15.b.

N-(6,7-Methylenedioxyquinolin-4-yl)-N-[1-[(t-butyldimethylsilanyloxy)-methyl]-N-2-dimethylaminoethyl]]-2-iodo-4,5-dimethoxybenzamide. Prepared from 4-[N-4-[2-(N,N-dimethylamino)-1-[(t-butyldimethylsilanyloxy)methyl]-ethyl]amino-6,7-methylenedioxyquinoline (0.48 mg, 1.2 mol) in 55% yield with a reaction time of 18 h, from the acid chloride prepared using 5.9 mmol of oxalyl chloride and 2.4 mmol of 2-iodo-5,6-dimethoxybenzoic acid. Compound 8j had: IR (CHCl$_3$) 1656; $^1$H NMR (CDCl$_3$) [unresolved atropisomers in a an apparent 57:43 ratio ar r.t.] major atropisomer δ 0.01 (s, 6H), 0.84 (s, 9H), 2.34 (s, 6H), 2.55 (m, 1H), 2.85 (m, 1H); 3.43 (s, 3H), 3.71(s, 3H) 3.86-4.04 (m, 3H), 6.12 (s, 2H), 6.56 (s, 1H), 7.29-7.31 (s, 1H), 7.67 (d, 1H, J=5.0), 8.00 (s, 1H), 8.59 (d, 1H, J=4.4); minor atropisomer δ 0.17 (s, 6H), 0.96 (s, 9H), 2.15 (s, 6H), 2.55 (m, 1H), 2.85 (m, 1H), 3.36 (s, 3H), 3.72 (s, 3H) 3.86-4.04 (m, 3H), 6.13 (s, 2H), 6.53(s, 1H), 7.00 (s, 1H), 7.31 (s, 1H), 7.51 (d, 1H, J=4.8), 8.25 (s, 1H), 8.55 (d, 1H, J=5.2).

EXAMPLE 16.b.

N-(6,7-Methylenedioxyquinolin-4-yl)-N-[(2,3-dihydroxy)propyl]-2-iodo-5,6-dimethoxybenzamide. Prepared from 4-[N-(2,2-dimethyl-[1,3]dioxolan-4-yl)methyl]amino-6,7-methylenedioxyquinoline (290 mg, 0.9 mmol) in 47% yield with a reaction time of 12 h, from the acid chloride prepared using 30 mmol of oxalyl chloride and 13 mmol of 2-iodo-5,6-dimethoxybenzoic acid. The acid chloride was added as a methylene chloride solution to a solution of 7k in 125 mL of DME containing triethylamine (3.04 g 30.1 mmol). Compound 8k had: IR (CHCl$_3$) 1653; $^1$H NMR (CDCl$_3$) δ 1.21 (s, 3H), 1.33 (s, 3H), 3.33 (s, 3H), 3.76 (s, 3H), 3.94 (m, 3H), 4.61 (m, 2H), 6.18 (s, 1H), 6.39 (s, 1H), 7.05 (s, 1H), 7.31 (d, 1H, J=4.8), 7.46 (s, 1H), 7.49 (s, 1H), 8.61 (d, 1H, J=4.8); $^{13}$C NMR (CDCl$_3$) δ 25.6, 26.9, 55.6, 56.1, 56.4, 68.2, 73.2, 82.8, 98.2, 98.7, 102.4, 106.1, 110.3, 120.7, 121.7, 124.1, 133.3, 147.5, 148.0, 148.8, 149.5, 150.0, 151.5, 152.3, 167.8; HRMS calcd for $C_{25}H_{25}N_2O_7IH$: 593.0785; found 593.0802.

EXAMPLES 13.c.-15.c.

The intermediate alcohols from Examples 13.d.-15.d. were converted to their corresponding silyl ethers using the following general procedure.

A mixture of the 4-amino-6,7-methylenedioxyquinoline derivative (1.0 mmole equiv.), imidazole (1.1 mmol equiv.) and t-butyldimethylsilyl chloride (1.2 mmol equiv.) in DMF (15 mL per mmol equiv) was stirred at room temperature for 6 h. DMF was removed in vacuo, water was added to residue, and solid was filtered and dried.

EXAMPLE 13.c.

4-[N-[2-(t-Butyldimethylsilanyloxy)]ethyl]amino-6,7-methylenedioxyquinoline. Prepared from N-(6,7-Methylenedioxyquinolin-4-yl)ethanolamine in 48.7% yield; mp 215-216° C.; $^1$H NMR (DMSO-d$_6$) δ 0.01 (s, 6H), 0.85 (s, 9H), 3.39 (dd, 2H, J=6, 12), 3.80 (t, 2H, J=6.2), 6.14 (s, 2H), 6.42 (d, 1H, J=5.4), 7.12 (s, 1H), 7.60 (s, 1H), 8.18 (d, 1H, J=4.8).

EXAMPLE 14.c.

4-[N-[2-[2-(t-Butyldimethylsilanyloxy)ethoxy]ethyl]ethyl]amino-6,7-methylenedioxyquinoline. Prepared from 2-[2-[N-(6,7-Methylenedioxyquinolin-4-yl)]amino]ethoxyethanol in 39% yield (overall yield from 5); $^1$H NMR (CDCl$_3$) δ 0.1 (s, 6H), 0.92 (s, 9H), 3.64-3.69 (m, 4H), 3.84 (d, 2H, J=5.2,), 3.93 (d, 2H, J=5.2), 6.15 (s, 2H), 6.56 (d, 1H, J=6.4), 7.42 (s, 1H), 7.82 (s, 1H), 8.18 (d, 1H, J=6.4).

EXAMPLE 15.c.

4-[N-4-[2-(N,N-dimethylamino)-1-[(t-butyldimethylsilanyloxy)methyl]-ethyl]amino-6,7-methylenedioxyquinoline.

Prepared from 2-[[N-(6,7-Methylenedioxyquinolin-4-yl)]amino]-3-(N,N-dimethylamino)propanol in 25% yield (overall yield from 5); $^1$H NMR (CDCl$_3$) [unresolved atropisomers in a an apparent 57:43 ratio at r.t.] major atropisomer δ 0.07(s, 6H), 0.92-0.94 (s, 9H), 2.24 (s, 6H), 2.45-2.55 (m, 2H), 3.60-4.05 (m, 3H), 5.40 (d, 1H), 6.09 (s, 2H), 6.45 (d, 1H, J=6.4), 7.02 (s, 1H), 7.30 (s, 1H), 8.18 (d, 1H, J=6.4); minor atropisomer δ 0.09 (s, 6H), 0.94 (s, 9H), 2.30 (s, 6H), 2.45-2.55 (m, 2H), 3.60-4.05 (m, 3H), 5.40 (d, 1H), 6.0 (s, 2H), 6.45 (d, 1H, J=6.4), 7.02 (s, 1H), 7.30 (s, 1H), 8.18 (d, 1H, J=6.4)

EXAMPLE 16.c.

4-[N-(2,2-dimethyl-[1,3]dioxolan-4-yl)methyl]amino-6,7-methylenedioxyquinoline. A mixture of 3-[[N-(6,7-Methylenedioxyquinolin-4-yl)]amino]-1,2-propandiol (500 mg, 1.9 mmol), p-toluenesulfonic acid (5 mg, 0.02 mg) in DMF (20 mL) and 2,2-dimethoxypropane (5 mL), was heated to 80° C. and stirred at this temperature for 18 h. To the cooled solution was added 1 mL of pyridine and the solvent evaporated in vacuo. The crude material was chromatographed in 96:4 chloroform-methanol to give 466 mg of the acetonide, in 81% yield; mp 219-221° C.; $^1$H NMR(CD$_3$OD) δ 1.35 (s, 3H), 1.38 (s,3H), 3.74 (m, 3H), 4.19 (m, 1H), 4.49 (m, 1H), 6.28 (s, 2H), 6.94 (d, 1H, J=7.2), 7.20 (s, 1H), 7.74 (s, 1H), 8.24 (d, 1H, J=7.2); $^{13}$C NMR (CD$_3$OD) δ 23.5, 25.1,45.0, 66.0, 73.6, 96.5, 97.7, 97.8, 103.1, 109.1, 112.2, 135.8, 138.6, 148.4, 153.3, 155.3; HRMS calcd for C$_{16}$H$_{18}$N$_2$O$_4$: 302.1267; found 302.1267.

EXAMPLES 13.d-16.d.

The intermediate 4-amino-6,7-dimethoxyquinoline derivatives used in Examples 13.c-16.c. were prepared using the following general procedure.

4-Chloro-6,7-methylenedioxyquinoline was stirred in refluxing phenol (5.5 mol equiv.) for 2.5 h. The temperature was lowered to 100° C. and the primary amine (1.0 mol equiv.) added with stirring. The reaction was then allowed to stir at 100° C. for several hours, and the phenol removed by Kugelrohr distillation under reduced pressure. In the case of those derivatives that have an alkylamine incorporated in their structure, the residue was partitioned between CHCl$_3$ and 10% NaOH. The aqueous layer was repeatedly separated with CHCl$_3$. All of the CHCl$_3$ solutions (initial partition and extracts) were combined and dried (MgSO$_4$). Other 4-amino-6,7-methylenedioxyquinoline derivatives were purified by column chromatography.

EXAMPLE 13.d.

N-(6,7-Methylenedioxyquinolin-4-yl)ethanolamine was prepared from ethanolamine (0.6 g, 10 mmol) from in 53.9% yield with a reaction time of 24 h: mp 233-234° C.; $^1$H NMR (DMSO-d$_6$); δ 3.51 (dd, 2H, J=10.4, 6.), 3.69 (t, 2H, J=6.0), 6.27 (s, 2H), 6.72 (d, 1H, J=7.0), 7.37 (s, 1H), 8.12 (s, 1H), 8.29 (d, 1H, J=7.0); $^{13}$C NMR (DMSO-d$_6$); 46.5, 59.5, 98.6, 98.8, 100.3, 103.8, 113.2, 137.6, 141.0, 148.2, 152.8, 155.0; HRMS calcd for C$_{12}$H$_{12}$N$_2$O$_3$H: 232.0848; found 232.0881.

EXAMPLE 14.d.

2-[2-[N-(6,7-Methylenedioxyquinolin-4-yl)]amino]ethoxyethanol was prepared from 2-[2-(hydroxyethyl)ethoxy]ethylamine (0.76 g, 7.2 mmol) with a reaction time of 18 h. The compound was converted directly to its t-butyldimethylsilanyloxy derivative in Example 14.c. above.

EXAMPLE 15.d.

2-[[N-(6,7-Methylenedioxyquinolin-4-yl)]amino]-3-(N,N-dimethylamino)propanol was prepared from 1-(hydroxymethyl)-2-(N,N-dimethylethylenediamine (1.13 g, 9.6 mmol) with a reaction time of 48 h. The compound was converted directly to its t-butyldimethylsilanyloxy derivative in Example 15.c. above.

EXAMPLE 16.d.

3-[[N-(6,7-Methylenedioxyquinolin-4-yl)]amino]-1,2-propandiol was prepared from 3-amino-1,2-propanediol (1.32 g, 14.5 mmol) in 34% yield with a reaction time of 24 h: mp 213-217° C. (dec.); $^1$H NMR (CD$_3$OD) δ 3.67 (m, 5H), 6.26 (s, 2H), 6.87 (d, 1H, J=7.2), 7.19 (s, 1H), 7.71 (s, 1H), 8.21 (d, 1H, J=7.2); $^{13}$C NMR (CD$_3$OD) δ 45.7, 63.1, 69.4, 96.8, 97.4, 97.8, 103.0, 112.3, 136.1, 138.9, 148.2, 153.0, 155.0; HRMS calcd for C$_9$H$_7$N$_3$O$_2$: 262.0954; found 262.0954.

EXAMPLE 17

8,9-Dimethoxy-2,3-methylenedioxy-5-[2-(N,N-dimethylamino)ethyl]-5,6-dihydro-dibenzo[c,h]1,6-naphthyridine (4a): To a solution of 8,9-dimethoxy-2,3-methylenedioxy-5-[2-(N,N-dimethylamino)ethyl]-5H-dibenzo[c,h]1,6-naphthyridin-6-one (160 mg, 0.38 mmol) in THF (650 mL) was added LiAlH$_4$ (75 mg, 2.0 mmol), and the mixture was stirred under nitrogen at reflux. After 2 h, an additional 2.0 mmol of LiAlH$_4$ was again added. The reaction was refluxed for an additional 3h, then allowed to cool to room temperature. The reaction was quenched by the sequential addition of water (5 drops), 10% NaOH (5 drops), and water (5 drops). The mixture was filtered through Celite and evaporated, and the crude mixture was chromatographed on silica in 98:2 chloroform-methanol, to give 132 mg of the reduced product, in 85% yield; mp 271-273° C. (dec.); $^1$H NMR (CDCl$_3$) δ 2.24 (s, 6H), 2.58 (t, 2H, J=6.8), 3.12 (t, 2H, J=6.8), 3.97 (s, 3H), 4.02 (s, 3H), 4.27 (s, 2H), 6.13 (s, 2H), 6.79 (s, 1H), 7.38 (s, 2H), 7.61 (s, 1H), 9.05 (s, 1H); $^{13}$C NMR (CDCl$_3$) δ 46.0, 50.6, 51.2, 56.2, 26.3, 58.4, 99.6, 101.7, 105.7, 106.6, 110.0, 120.7, 123.1, 124.8, 131.1, 144.1, 146.9, 148.0, 149.0, 149.4, 149.8, 150.2; HRMS calcd for C$_{23}$H$_{25}$N$_3$O$_4$: 407.1845; found 407.1848.

EXAMPLE 18

8,9-Dimethoxy-2,3-methylenedioxy-5-[2-(N,N-dimethylamino)-1-methylethyl]-5,6-dihydro-dibenzo[c,h]1,6-naphthyridine. The title compound was prepared as follows. 8,9-Dimethoxy-2,3-methylenedioxy-5-[2-(N,N-dimethylamino)-1-methylethyl]-5H-dibenzo[c,h]1,6-naphthyridin-6-one (80 mg, 0.18 mmol; Example 7) in THF (150 mL) was added to LiAlH$_4$ (50 mg, 1.3 mmol), and the mixture was stirred under nitrogen at reflux for 4 h. The reaction was quenched by the sequential addition of water (5 drops), 10% NaOH (5 drops), and water (5 drops). The mixture was filtered through Celite and evaporated, and the crude mixture was chromatographed on silica in 1.0% methanol in chloroform to give 35 mg of the reduced product, in 45.4% yield; mp 153-154° C.; $^1$H NMR (CDCl$_3$) δ 1.16 (d, 3H, J=8), 2.38 (dd, 2H, J=12.2, 8.0), 3.68-3.80 (m, 1), 3.88 (s, 3H), 4.24 (s, 2H), 6.16 (s, 2H), 6.64 (s, 1H), 7.24 (s, 1H), 7.40 (s, 2H), 7.62 (s, 1H), 8.88 (s, 1H); $^{13}$C NMR (CDCl$_3$) δ: 17.7, 45.6, 46.0, 56.2, 56.4, 57.8, 64.2, 100.1, 101.7, 105.8, 106.4, 108.5, 120.5, 120.6, 123.6, 126.9, 143.4, 146.6, 147.7, 148.9, 149.5, 149.6, 150.0; HRMS calcd for $C_{24}H_{27}N_3O_4H$ 422.2002; found 422.2081.

EXAMPLE 19

8,9-Dimethoxy-2,3-methylenedioxy-5-[2-(N,N-diethylamino)ethyl]-5H-dibenzo[ch]1,6-naphthyridin-6-one A mixture of N-(6,7-Methylenedioxyquinolin-4-yl)-N-[2-(N,N-diethylamino)ethyl]-2-iodo-4,5-dimethoxybenzamide (577 mg, 1.0 mmol), $Pd(OAc)_2$ (45, 0.2 mmol), $P(o-tolyl)_3$ (122 mg, 0.4 mmol), and silver carbonate (550 mg, 2.0 mmol) was heated to reflux in DMF (30 mL) and stirred under nitrogen for 30 minutes. The reaction mixture was cooled to room temperature, diluted with chloroform and filtered though a bed of Celite. The filter was washed well with 90:10 chloroform-methanol. Then the solvent was removed under reduced pressure and the resulting residue was chromatographed on silica gel using 99:1 chloroform-methanol to give the cyclized compound (250 mg) as a white solid, in 56% yield; mp 221-223° C. (dec.); IR ($CHCl_3$) 3029, 3009, 2971, 2939, 2910, 1648, 1611, 1570, 1523, 1497, 1467, 1386, 1310, 1267, 1248, 1217, 1213, 1166, 1040; $^1H$ NMR ($CDCl_3$) δ 0.95 (t, 6H, J=7.0), 2.80 (1, 4H, J=7.0), 3.04 (t, 2H, J=6.7), 4.06 (s, 3H), 4.13 (s, 3H), 4.63 (t, 2H, J=6.7), 6.17 (s, 2H), 7.46 (s, 1H), 7.68 (s, 1H), 7.90 (s, 1H), 7.96 (s, 1H), 9.37 (s, 1H); $^{13}C$ NMR ($CDCl_3$) δ 12.0, 47.6, 49.6, 51.7, 56.3, 101.4, 102.0, 102.2, 107.0, 108.9, 111.8, 115.0, 119.5, 127.7, 141.1, 143.5, 147.3, 147.7, 149.9, 150.3, 154.2, 164.2; HRMS calcd for $C_{25}H_{27}O_5N_3H$: 450.2030; found: 450.2032.

a. 4-[[2-(Diethylamino)ethyl]amino]-6,7-methylenedioxyquinoline. 4-Chloro-6,7-methylenedioxyquinoline. (1.0 g, 4.83 mmol) was stirred in boiling phenol for 2.5 hours. Then the mixture was cooled to 140° C. and N,N-diethylethylenediamine (1.16 g, 10.0 mmol) was added. The reaction mixture was stirred at this temperature for 18 hours, and then phenol was removed on the Kugelrohr. The crude residue was partitioned between dilute HCl (100 mL) and chloroform (100 mL), and the organic phase was extracted with dilute HCl (100 mL). The combined aqueous phases were washed with chloroform (100 mL) and then basified with 30% NaOH, extracted into chloroform (3×100 mL), dried ($MgSO_4$) and evaporated to give 793 mg as a white solid, in 58% yield; mp 201-202° C.; IR ($CHCl_3$) 3364, 2967, 2936, 2907, 2875, 1620, 1546, 1466, 1295, 1222, 1218, 1210, 1152, 1041; $^1H$ NMR ($CDCl_3$) δ 1.09 (t, 6H, J=7.2), 2.61 (q, 4H, J=7.2), 2.82 (t, 2H, J=5.8), 3.26 (m, 2H), 5.71 (br, 1H), 6.08 (d, 2H), 6.35 (d, 1H, J=5.2), 7.03 (s, 1H), 7.31 (s, 1H), 8.40 (d, 1H, J=5.2); $^{13}C$ NMR ($CDCl_3$) δ 12.2, 40.1, 46.7, 51.0, 96.1, 99.0, 101.5, 106.7, 114.5, 146.5, 146.7, 149.1, 149.6, 149.9; HRMS calcd for $C_{16}H_{21}O_2N_3$: 287.1634; found: 287.1631.

b. N-(6,7-Methylenedioxyquinolin-4-yl)-N-[2-(N,N-diethylamino)ethyl]-2-iodo-4,5-dimethoxybenzamide. Oxalyl chloride (1.12 g, 8.8 mmol) was added to a solution of 2-Iodo-4,5-dimethoxybenzoic acid (820 mg, 2.6 mmol; see above) in anhydrous methylene chloride (40 mL) and the stirred mixture was refluxed for 4 hours. The mixture was then concentrated to dryness under reduced pressure. The acid chloride was dissolved in 40 mL of methylene chloride and added to a solution of 4-[[2-(Diethylamino)ethyl]amino]-6,7-methylenedioxyquinoline (640 mg, 2.2 mmol), and triethylamine (2.2 g, 22 mmol) in methylene chloride (50 mL) and the resulting mixture was stirred at reflux under nitrogen for 2 hours. The reaction mix was cooled and washed with a saturated solution of sodium bicarbonate (3×75 mL), and extracted into dilute HCl (4×100 mL). The aqueous extract was then neutralized with 30% NaOH and extracted with $CHCl_3$ (4×100 mL), washed with brine (100 mL), dried ($MgSO_4$) and evaporated, yielding 1.1 g as a sticky semisolid glue, in 86% yield; $^1H$ NMR ($CDCl_3$) δ 0.96 (t, 6H, J=7.2), 2.54 (q, 4H, J=7.2), 2.82 (m, 2H), 3.29 (s, 3H), 3.71 (s, 3H), 3.92 (m, 1H), 4.46 (m, 1H), 6.12 (s, 2H), 6.37 (s, 1H), 7.00 (s, 1H), 7.27 (d, 1H, J=4.8), 7.33 (s, 1H), 7.39(s, 1H), 8.52 (d, 1H, J=4.8); $^{13}C$ NMR($CDCl_3$) δ 11.8, 47.1, 47.5, 50.7, 55.5, 56.1, 82.7, 98.5, 102.2, 106.7, 110.6, 120.1, 121.8, 122.7, 133.7, 146.3, 148.1, 148.3, 148.5, 149.0, 149.7, 151.0, 170.0; HRMS calcd for $C_{25}H_{28}O_5N_3IH$: 578.1153; found: 578.1153.

The intermediate 4-Chloro-6,7-methylenedioxyquinoline was prepared as described above.

The intermediate 2-Iodo-4,5-dimethoxybenzoic acid was prepared as follows.

c. 2-Iodo-4,5-dimethoxybenzoic acid. A mixture of 2-amino-4,5-dimethoxybenzoic acid (10.0 g, 50 mmol) in water (100 mL) and concentrated $H_2SO_4$ (14 mL) was cooled to 5° C. and a solution of $NaNO_2$ (3.5 g) in water (12.5 mL) was added in a dropwise fashion while maintaining the temperature between 0-5° C. Follwing the addition the mixture was stirred at this temperature for an additional 30 minutes. Then a solution of KI (13.0 g, 78.3 mmol) in water (20.5 mL) and concentrated $H_2SO_4$ (4.4 mL) was rapidly added and the flask was transferred to an oil bath that had been preheated to 105° C. The mixture was stirred for 30 minutes following the onset of reflux. The flask was then cooled and extracted into chloroform (3×300 mL), washed with water (3×200 mL), dilute HCl (200 mL), and brine (200 mL), then the solvent was dried ($Na_2SO_4$) and evaporated, and the residue was chromatographed in chloroform to give 13.1 g as a white solid, in 84% yield; mp 162.0-163.5° C. (lit. mp 159-160° C.); $^1H$ NMR ($CDCl_3$) δ 3.93 (s, 3H), 3.95 (s, 3H), 7.46 (s, 1H), 7.65 (s, 1H); $^{13}C$ NMR ($CDCl_3$) δ56.1, 56.4, 85.8, 114.8, 124.3, 124.5, 148.8, 152.7, 170.5.

EXAMPLE 22

Using procedures similar to those described above, the compound 2,3-dimethoxy-8,9-methylenedioxy-11-[2-(4-methylpiperazin-1-yl)ethyl]-11H-5,6,11-triazachrysen-12-one was also prepared.

EXAMPLE 21

Using procedures similar to those described above, the following compounds of the invention were also prepared: 8,9-dimethoxy-2,3-methylenedioxy-5-(2-piperidinoethyl)-5H-dibenzo[c,h]1,6-naphthyridin-6-one; 8,9-dimethoxy-2,3-methylenedioxy-5-[2-(4-benzylpiperazin-1-yl)ethyl]-5H-dibenzo[c,h]1,6-naphthyridin-6-one; 8,9-dimethoxy-2,3-methylenedioxy-5-formylmethyl-5H-dibenzo[c,h]1,6-naphthyridin-6-one; and 8,9-dimethoxy-2,3-methylenedioxy-5-[2-(N-methylamino)ethyl]-5H-dibenzo[c,h]1,6-naphthyridin-6-one.

EXAMPLE 22

The following illustrate representative pharmaceutical dosage forms, containing a compound of formula I ('Compound X'), for therapeutic or prophylactic use in humans.

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0–7.5) | q.s. |
| Water for injection | q.s. ad 1 mL |

| (v) Injection 2 (10 mg/ml) | mg/ml |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0–7.5) | q.s. |
| Water for injection | q.s. ad 1 mL |

| (vi) Injection 3 (1 mg/ml) | mg/ml |
|---|---|
| 'Compound X' (free base form) | 1.0 |
| Citric Acid | 0.1% |
| D5W | q.s. ad 1 mL |

| (vii) Aerosol | mg/can |
|---|---|
| 'Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method of inhibiting breast cancer cell growth, comprising administering to the mammal an amount of a compound of formula I

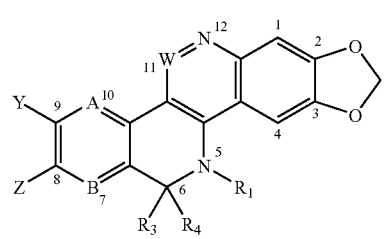

wherein:
A and B are independently N or CH;
W is N or CH;
$R_3$ and $R_4$ are each independently H, $(C_1-C_6)$alkyl, or substituted $(C_1-C_6)$alkyl, or $R_3$ and $R_4$ together are =O, =S, =NH or =N—$R_2$;
Y and Z are independently hydroxy, $(C_1-C_6)$alkoxy, substituted $(C_1-C_6)$alkoxy, $(C_1-C_6)$alkanoyloxy, substituted $(C_1-C_6)$alkanoyloxy, —O—P(=O)(OH)$_2$, or —O—C(=O)NR$_c$R$_d$; or Y and Z together with the ring carbon atoms to which they are attached form an alkylenedioxy ring with from 5 to 7 ring atoms;
$R_1$ is a —$(C_1-C_6)$alkyl substituted with one or more solubilizing groups;
$R_2$ is $(C_1-C_6)$alkyl or substituted $(C_1-C_6)$alkyl; and
$R_c$ and $R_d$ are each independently $(C_1-C_6)$alkyl or substituted $(C_1-C_6)$alkyl; or $R_c$ and $R_d$ together with the nitrogen to which they are attached form a N'—{$(C_1-C_6)$alkyl}piperazino, pyrrolidino, or piperidino ring, which ring can optionally be substituted with one or more aryl, heteroaryl, or heterocycle;
or a pharmaceutically acceptable salt thereof;
effective to inhibit breast cancer cell growth in the mammal.

2. A method for producing an antipsoritic effect in a mammal, comprising administering to the mammal an amount of a compound of formula I

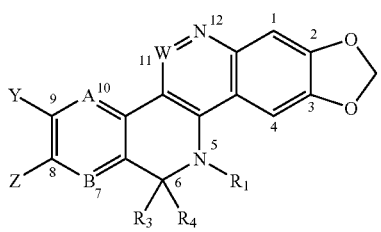

wherein:
A and B are independently N or CH;
W is N or CH;
$R_3$ and $R_4$ are each independently H, $(C_1-C_6)$alkyl, or substituted $(C_1-C_6)$alkyl, or $R_3$ and $R_4$ together are =O, =S, =NH or =N—$R_2$;
Y and Z are independently hydroxy, $(C_1-C_6)$alkoxy, substituted $(C_1-C_6)$alkoxy, $(C_1-C_6)$alkanoyloxy, substituted $(C_1-C_6)$alkanoyloxy, —O—P(=O)(OH)$_2$, or —O—C(=O)NR$_c$R$_d$; or Y and Z together with the ring carbon atoms to which they are attached form an alkylenedioxy ring with from 5 to 7 ring atoms;
$R_1$ is a —$(C_1-C_6)$alkyl substituted with one or more solubilizing groups;
$R_2$ is $(C_1-C_6)$alkyl or substituted $(C_1-C_6)$alkyl; and
$R_c$ and $R_d$ are each independently $(C_1-C_6)$alkyl or substituted $(C_1-C_6)$alkyl; or $R_c$ and $R_d$ together with the nitrogen to which they are attached form a N'—{$(C_1-C_6)$alkyl}piperazino, pyrrolidino, or piperidino ring, which ring can optionally be substituted with one or more aryl, heteroaryl, or heterocycle;
or a pharmaceutically acceptable salt thereof;
effective to produce an antipsoritic effect in the mammal.

3. The method of claim 1, wherein the compound of formula I is a compound of formula II

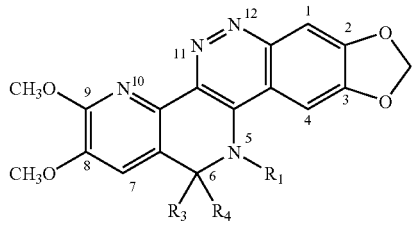

or a pharmaceutically acceptable salt thereof.

4. The method of claim 1, wherein the compound of formula I is a compound of formula III

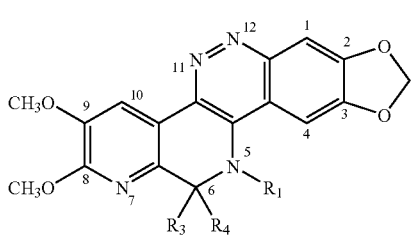

or a pharmaceutically acceptable salt thereof.

5. The method of claim 1, wherein the compound of formula I is a compound of formula IV

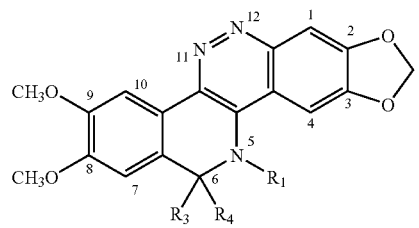

or a pharmaceutically acceptable salt thereof.

6. The method of claim 1, wherein the compound of formula I is a compound of formula V

V or a pharmaceutically acceptable salt thereof.

7. The method of claim 1, wherein the compound of formula I is a compound of formula VI

VI or a pharmaceutically acceptable salt thereof.

8. The method of claim 1, wherein the compound of formula I is a compound of formula VII

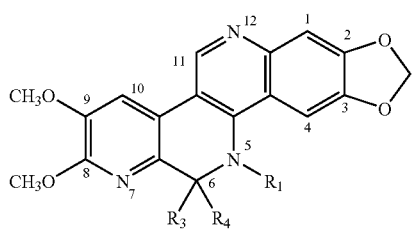

or a pharmaceutically acceptable salt thereof.

9. The method of claim 1, wherein the compound of formula I is a compound of formula VIII

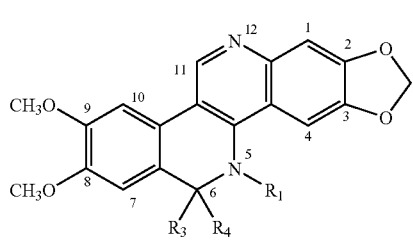

or a pharmaceutically acceptable salt thereof.

10. The method of claim 1, wherein the compound of formula I is a compound of formula IX

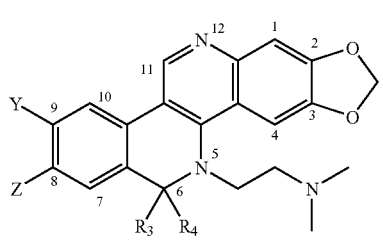

or a pharmaceutically acceptable salt thereof.

11. The method of claim 1, wherein the compound of formula I is 8,9-Dimethoxy-2,3-methylenedioxy-5-[2-(N,N-dimethylamino)ethyl]-5H-dibenzo[c,h]1,6-naphthyridin-6-one; 8,9-Dimethoxy-2,3-methylenedioxy-5-[2-(N,N-diethylamino)ethyl]-5H-dibenzo[c,h]1,6-naphthyridin-6-one; 8,9-Dimethoxy-2,3-methylenedioxy-5-[2-(N-methylamino)ethyl]-5H-dibenzo[c,h]1,6-naphthyridin-6-one; or a pharmaceutically acceptable salt thereof.

12. The method of claim 1 wherein the compound of formula I is 8,9-dimethoxy-2,3-methylenedioxy-5-[2-(N,N-dimethylamino)ethyl]-5H-dibenzo [c,h]1,6-naphthyridin-6-one.

13. The method of claim 1 wherein the compound of formula I is 8,9-dimethoxy-2,3-methylenedioxy-5-[2-(N,N-diethylamino)ethyl]-5H-dibenzo-[c,h]1,6-naphthyridin-6-one.

14. The method of claim 1 wherein the compound of formula I is 8,9-dimethoxy-2,3-methylenedioxy-5-[2-(N-methylamino)ethyl]-5H-dibenzo[c,h]1,6-naphthyridin-6-one.

15. The method of claim 2, wherein the compound of formula I is a compound of formula II

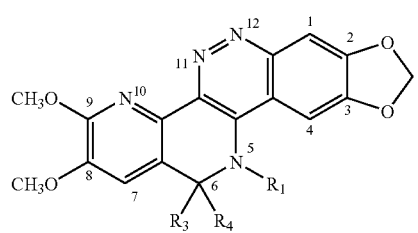

or a pharmaceutically acceptable salt thereof.

16. The method of claim 2, wherein the compound of formula I is a compound of formula III

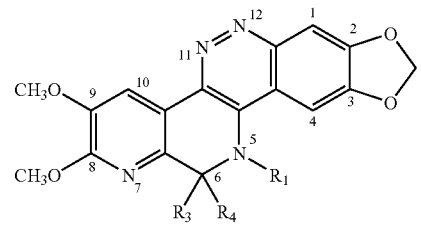

or a pharmaceutically acceptable salt thereof.

17. The method of claim 2, wherein the compound of formula I is a compound of formula IV

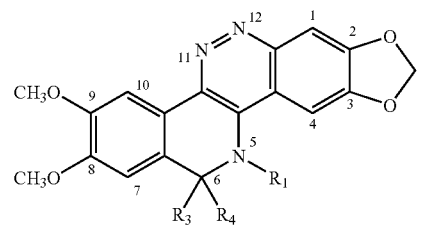

or a pharmaceutically acceptable salt thereof.

18. The method of claim 2, wherein the compound of formula I is a compound of formula V

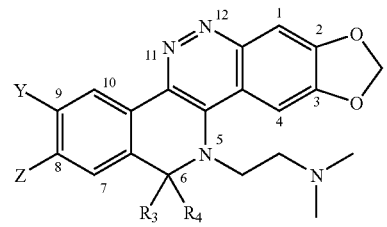

or a pharmaceutically acceptable salt thereof.

19. The method of claim 2, wherein the compound of formula I is a compound of formula VI

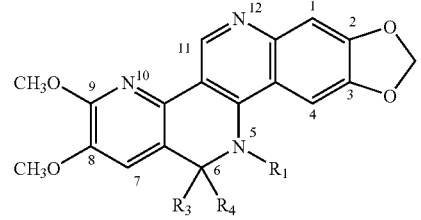

or a pharmaceutically acceptable salt thereof.

20. The method of claim 2, wherein the compound of formula I is a compound of formula VII

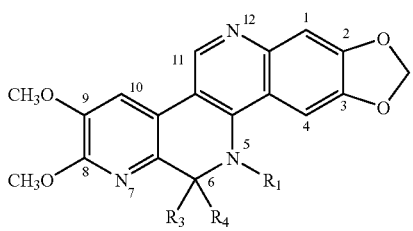

or a pharmaceutically acceptable salt thereof.

21. The method of claim 2, wherein the compound of formula I is a compound of formula VIII

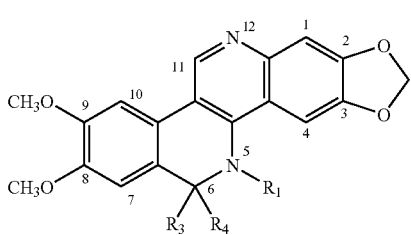

or a pharmaceutically acceptable salt thereof.

22. The method of claim 2, wherein the compound of formula I is a compound of formula IX

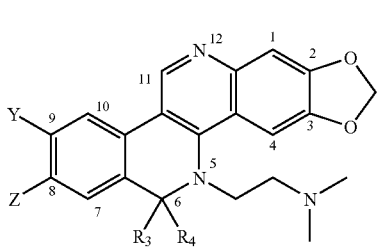

or a pharmaceutically acceptable salt thereof.

23. The method of claim 2, wherein the compound of formula I is 8,9-Dimethoxy-2,3-methylenedioxy-5-[2-(N,N-dimethylamino)ethyl]-5H-dibenzo[c,h]1,6-naphthyridin-6-one;8,9-Dimethoxy-2,3-methylenedioxy-5-[2-(N,N-diethylamino)ethyl]-5H-dibenzo[c,h]1,6-naphthyridin-6-one; 8,9-Dimethoxy-2,3-methylenedioxy-5-[2-(N-methylamino)ethyl]-5H-dibenzo[c,h]1,6-naphthyridin-6-one; or a pharmaceutically acceptable salt thereof.

24. The method of claim 2 wherein the compound of formula I is 8,9-dimethoxy-2,3-methylenedioxy-5-[2-(N,N-dimethylamino)ethyl]-5H-dibenzo[c,h]1,6-naphthyridin-6-one.

25. The method of claim 2 wherein the compound of formula I is 8,9-dimethoxy-2,3-methylenedioxy-5-[2-(N,N-diethylamino)ethyl]-5H-dibenzo-[c,h]1,6-naphthyridin-6-one.

26. The method of claim 2 wherein the compound of formula I is 8,9-dimethoxy-2,3-methylenedioxy-5-[2-(N-methylamino)ethyl]-5H-dibenzo[c,h]1,6-naphthyridin-6-one.

27. The compound 8,9-dimethoxy-2,3-methylenedioxy-5-[2-(N,N-dimethylamino)ethyl]-5H-dibenzo[c,h]1,6-naphthyridin-6-one or a pharmaceutically acceptable salt thereof.

28. The compound 8,9-dimethoxy-2,3-methylenedioxy-5-[2-(N,N-diethylamino)ethyl]-5H-dibenzo-[c,h]1,6-naphthyridin-6-one or a pharmaceutically acceptable salt thereof.

29. The compound 8,9-dimethoxy-2,3-methylenedioxy-5-[2-(N-methylamino)ethyl]-5H-dibenzo[c,h]1,6-naphthyridin-6-one or a pharmaceutically acceptable salt thereof.

30. A pharmaceutical composition comprising 8,9-dimethoxy-2,3-methylenedioxy-5-[2-(N,N-dimethylamino)ethyl]-5H-dibenzo[c,h]1,6-naphthyridin-6-one or a pharmaceutically acceptable salt thereof, and a pharmaceutically acceptable carrier.

31. A pharmaceutical composition comprising 8,9-dimethoxy-2,3-methylenedioxy-5-[2-(N,N-diethylamino)ethyl]-5H-dibenzo-[c,h]1,6-naphthyridin-6-one or a pharmaceutically acceptable salt thereof, and a pharmaceutically acceptable carrier.

32. A pharmaceutical composition comprising 8,9-dimethoxy-2,3-methylenedioxy-5-[2-(N-methylamino)ethyl]-5H-dibenzo[c,h]1,6-naphthyridin-6-one or a pharmaceutically acceptable salt thereof, and a pharmaceutically acceptable carrier.

* * * * *